United States Patent
Gonsalves et al.

(10) Patent No.: US 10,996,224 B2
(45) Date of Patent: May 4, 2021

(54) ASSESSING AND TREATING PRECURSOR PLASMA CELL DISORDERS

(71) Applicant: Mayo Foundation for Medical Education and Research, Rochester, MN (US)

(72) Inventors: Wilson I. Gonsalves, Rochester, MN (US); Shaji Kumar, Rochester, MN (US); K. Sreekumaran Nair, Rochester, MN (US); Vijay Ramakrishnan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/918,120

(22) Filed: Mar. 12, 2018

(65) Prior Publication Data
US 2018/0275132 A1    Sep. 27, 2018

Related U.S. Application Data

(60) Provisional application No. 62/474,221, filed on Mar. 21, 2017.

(51) Int. Cl.
| | |
|---|---|
| *C07H 21/04* | (2006.01) |
| *G01N 33/574* | (2006.01) |
| *A61K 45/06* | (2006.01) |
| *A61K 31/7105* | (2006.01) |

(52) U.S. Cl.
CPC ... *G01N 33/57496* (2013.01); *A61K 31/7105* (2013.01); *A61K 45/06* (2013.01); *G01N 33/57488* (2013.01)

(58) Field of Classification Search
None
See application file for complete search history.

(56) References Cited

U.S. PATENT DOCUMENTS

| 8,883,438 B2 | 11/2014 | Cantley |
| 2013/0183281 A1 | 7/2013 | Su et al. |
| 2016/0102087 A1 | 4/2016 | Hussain et al. |

OTHER PUBLICATIONS

Oliva, Stefania, et al. "Promises and Pitfalls in the use of PD-1/PD-L1 Inhibitors in Multiple Myeloma." Frontiers in immunology 9 (2018):2749.*
Rannsenthaler, Christina, et al. "Prevalence of symptoms in patients with multiple myeloma: a systematic review and meta-analysis." European Journal of Haematology 97.5 (2016): 416-429.*
Gonsalves et al., "Glutamine-derived 2-hydroxyglutarate is associated with disease progression in plasma cell malignancies," JCI Insight, Jan. 2018, 3(1): 16 pages.
Kyle et al., "A long-term study of prognosis in monoclonal gammopathy of undetermined significance," N Engl J Med., Feb. 2002, 346: 564-569.
Kyle et al., "Clinical course and prognosis of smoldering (asymptomatic) multiple myeloma," N Engl J Med., Jun. 2007, 356:2582-2590.
Kyle et al., "Review of 1027 patients with newly diagnosed multiple myeloma," Mayo Clin Proc., Jan. 2003, 78: 21-33.
Wang et al., "Prognostic significance of 2-hydroxyglutarate levels in acute myeloid leukemia in China," PNAS, Oct. 2013, 110(42): 17017-17022.
Lonial et al., "Randomized Trial of Lenalidomide Versus Observation in Smoldering Multiple Myeloma," J. Clin. Oncology, Oct. 25, 2019, 38(11):1126-1137.
Mateos et al., "Lenalidomide plus Dexamethasone for High-Risk Smoldering Multiple Myeloma," N. Engl. J. Medicine, Aug. 1, 2013, 369(5):438-447.

\* cited by examiner

*Primary Examiner* — Kimberly Chong
(74) *Attorney, Agent, or Firm* — Fish & Richardson P.C.

(57) ABSTRACT

This document relates to materials and methods in assessing and treating mammals (e.g., humans) with precursor plasma cell (PC) disorders. Materials and methods for determining if a mammal (e.g., a mammal having a precursor plasma cell disorder) has an elevated level of 2-hydroxyglutarate (2-HG) that can be used to identify the precursor plasma cell disorder as likely to progress to a PC cancer (e.g., multiple myeloma) are provided. Materials and methods for treating a mammal having a precursor PC disorder at high risk of progressing to a PC cancer also are provided.

10 Claims, 13 Drawing Sheets
Specification includes a Sequence Listing.

ASSESSING AND TREATING PRECURSOR PLASMA CELL DISORDERS

CROSS-REFERENCE TO RELATED APPLICATIONS

This application claims the benefit of U.S. Provisional Application Ser. No. 62/474,221, filed Mar. 21, 2017. The disclosure of the prior application is considered part of (and is incorporated by reference in) the disclosure of this application.

STATEMENT REGARDING FEDERAL FUNDING

This invention was made with government support under DK100469 awarded by the National Institutes of Health. The government has certain rights in the invention.

BACKGROUND

1. Technical Field

This document relates to materials and methods for assessing and/or treating mammals (e.g., humans) having precursor plasma cell (PC) disorders. For example, this document provides materials and methods for determining if a mammal (e.g., a mammal having a precursor plasma cell disorder) has an elevated level of 2-hydroxyglutarate (2-HG) that can be used to identify the precursor plasma cell disorder as being likely to progress to a PC cancer (e.g., multiple myeloma). This document also provides materials and methods for treating a mammal having a precursor PC disorder at high risk of progressing to a PC cancer.

2. Background Information

Multiple myeloma (MM) is a devastating and fatal PC malignancy characterized by the proliferation of clonal PCs within the bone marrow, and is associated with end-organ damage such as renal failure, lytic bone destruction, anemia or hypercalcemia (Kyle et al. 2003 *Mayo Clin Proc.* 78:21-33). MM is preceded by asymptomatic precursor plasma cell disorders such as monoclonal gammopathy of undetermined significance (MGUS) and smoldering multiple myeloma (SMM). Both MGUS and SMM patients have an increased life-long risk of progression to MM; however, a diagnosis of MM is not made until patients experience overt end-organ damage. MGUS progresses to MM at a rate of 1% per year (Kyle et al. 2002 *N Engl J Med.* 346:564-569) whereas SMM has a much higher rate of progression of 10% per year for the first five years, 3% per year for the next 5 years and then 1% per year thereafter (Kyle et al. 2007 *N Engl J Med.* 356:2582-2590).

SUMMARY

In some cases, patients having precursor PC disorders do not receive treatment until they progress to overt MM and experience end organ damage. There is a need to be able to identify which precursor PC disorders are likely to progress to PC cancers, and to offer high-risk patients early therapy, while sparing low risk patients from the risk of toxicity from therapeutic intervention.

This document relates to materials and methods involved in assessing and/or treating mammals (e.g., humans) with precursor PC disorders (e.g., precursor PC disorders at high risk of progressing to a PC cancer). For example, this document provides materials and methods for determining if a mammal (e.g., a mammal having a precursor plasma cell disorder) having a precursor PC disorder has elevated levels of 2-HG that can be used to identify precursor PC disorders at high risk of progressing to a PC cancer (e.g., MM). This document also provides materials and methods for treating a mammal having a precursor PC disorder at high risk of progressing to a PC cancer.

For the purposes of this document, the term "high risk of progressing" refers to a precursor PC disorder (e.g., MGUS or SMM) with a short time to progression (TTP) to a PC cancer (e.g., MM). For example, a precursor PC disorder with a high risk of progressing to a PC cancer can have a TTP of less than about 12 months (e.g., less than about 11 months, less than about 10 months, less than about 9 months, less than about 8 months, less than about 7 months, or less than about 6 months). As described herein, humans having elevated levels of 2-HG in clonal PCs can have a high risk of progression from precursor PC disorders (e.g., SMM) to MM, and gas-chromatography mass-spectrometry (GC-MS) can be used to quantitate the amount of 2-HG in the bone marrow (BM) plasma and/or peripheral blood (PB) plasma of patients having MGUS or SMM to identify patients who are at high risk of progression to symptomatic MM. Also as described herein, the presence of elevated levels of 2-HG can indicate that a mammal (e.g., a human) has increased c-Myc expression.

Having the ability to determine risk of progression in patients having precursor PC disorders provides a unique and unrealized opportunity to initiate early therapy to slow or prevent the development of a PC cancer, rather than waiting to treat patients having precursor PC disorders until after a PC cancer has developed.

In general, one aspect of this document features a method for treating a precursor PC disorder in a mammal. In some cases, method includes, or consists essentially of, identifying a mammal as having an elevated level of 2-HG within a biological sample from the mammal, and administering a PC cancer treatment to the mammal under conditions where the development of a symptom of a PC cancer (e.g., bone pain, nausea, constipation, loss of appetite, mental fogginess or confusion, fatigue, frequent infections, weight loss, weakness or numbness in your legs, excessive thirst, and/or lower extremity edema and/or swelling) is slowed or prevented. In some cases, the method includes, or consists essentially of, identifying a mammal as having an elevated level of 2-HG within a biological sample from the mammal, and administering a PC cancer treatment to the mammal under conditions where the development of a complication associated with a PC cancer (e.g., frequent infections, bone pain, thinning bones, broken bones, kidney failure, anemia, thrombocytopenia, neutropenia, and/or hypercalcemia) is slowed or prevented. The PC treatment can be bortezomib, carfilzomib, ixazomib, thalidomide, lenalidomide, pomalidomide melphalan, vincristine, cyclophosphamide, etoposide, doxorubicin, bendamustine, prednisone, dexamethasone, stem cell transplantation, radiation therapy, daratumumab, elotuzumab, chimeric antigen receptor T cell therapy, and/or allogeneic stem cell transplantation. The method also can include administering a c-Myc inhibitor to the mammal. The c-Myc inhibitor can be a siRNA. The c-Myc inhibitor can be an inhibitor of glutamine metabolism (e.g., a glutaminase inhibitor). The mammal can be a human. The precursor PC disorder can be MGUS or SMM. The PC cancer can be MM. The biological sample can be PB plasma or BM plasma. When the biological sample is PB plasma, the elevated level of 2-HG can be greater than 0.70 μM. When the biological sample is BM plasma, the elevated level of 2-HG can be greater than 0.30 μM.

In another aspect, this document features a method for assessing a precursor PC disorder. The method includes, or consists essentially of, detecting the level of 2-HG in a biological sample from a mammal, and identifying said mammal as having a precursor PC disorder at high risk of progressing to a PC cancer based at least in part on an elevated level of 2-HG The mammal can be a human. The precursor PC disorder can be MGUS or SMM. The PC cancer can be MM. The biological sample can be PB plasma or BM plasma. When the biological sample is PB plasma, the elevated level of 2-HG can be greater than 0.70 μM. When the biological sample is BM plasma, the elevated level of 2-HG can be greater than 0.30 μM. The precursor PC disorder at high risk of progressing to a PC cancer can have a time to progression of less than about 12 months.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
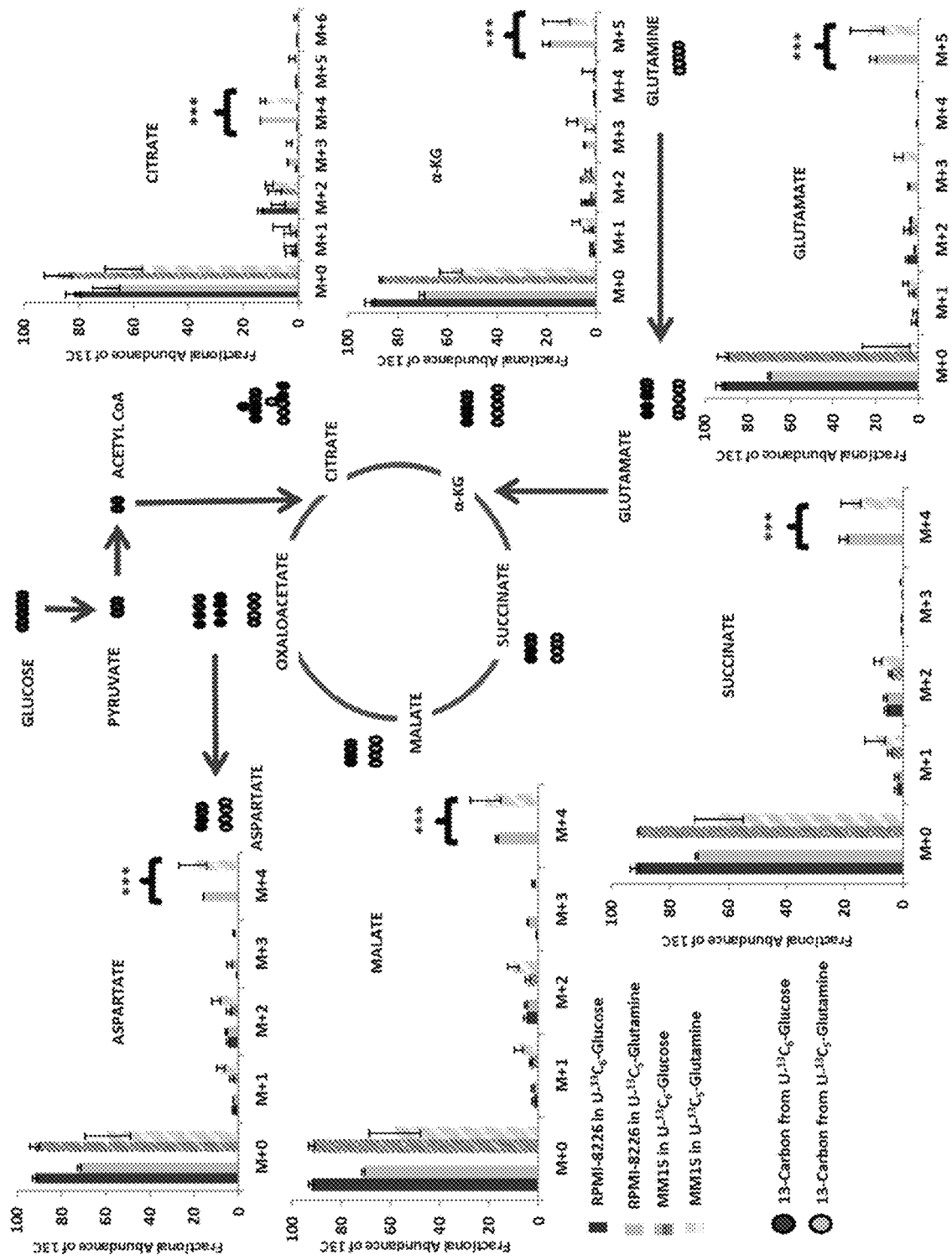
FIG. 1A is a mass isotopomer distribution of the various TCA cycle intermediates after incubation of MM1S and RPMI-8226 HMCLs in cell culture media containing either U-$^{13}C_5$-Glutamine or U-$^{13}C_6$-Glucose. The (m+4) or (m+5) isotopomers highlighted in lighter grey circles represent the isotopomer derived from U-$^{13}C_5$-Glutamine and the (m+2) isotopomers highlighted in darker grey circles are derived from U-$^{13}C_6$-Glucose. The unlabeled TCA cycle intermediates represented by (m+0) are highlighted in black circles.

This document provides materials and methods for assessing mammals (e.g., humans) having precursor PC disorders (e.g., MGUS and SMM). In some cases, this document provides materials and methods for detecting the presence of an elevated level of oncometabolite (e.g., 2-HG) within a biological sample from a mammal having a precursor PC disorder. As described herein, the presence of an elevated level of an oncometabolite can indicate that a mammal (e.g., a human) has a precursor PC disorder that may be at high risk of progressing to a PC cancer (e.g., MM). For example, a SMM patient having greater than about 0.30 µM 2-HG as measured in BM plasma and/or greater than about 0.70 µM 2-HG as measured in PB plasma can be at high risk of having a condition that can progress to MM. Also as described herein, the presence of elevated levels of 2-HG can indicate that a mammal (e.g., a human) may have increased c-Myc expression. This document also provides materials and methods for treating mammals having a precursor PC disorder. For example, this document provides materials and methods to treat a mammal (e.g., human) having a precursor PC disorder. In some cases, one or more MM treatments can be administered to a human having a precursor PC disorder where the human has elevated level of 2-HG Treating a precursor PC disorder can be effective to slow or prevent progression of the precursor PC disorder to a PC cancer. For example, the administered MM treatment(s) can slow or prevent the development of one or more symptoms associated with a PC cancer and/or the development of one or more complications associated with a PC cancer.

The term "elevated level" as used herein with respect to a level of an oncometabolite (e.g., 2-HG) refers to any level that is greater than the median level of the oncometabolite (e.g., 2-HG) typically observed in a sample (e.g., a control sample) from one or more mammals (e.g., humans) having a precursor PC disorder. Control samples can include, without limitation, samples from mammals with, MGUS, SMM, solitary plasmacytoma of bone, extramedullary plasmacytoma, primary amyloidosis, light chain deposition disease, paraproteinemia, and heavy-chain disease. In some cases, an elevated level of 2-HG can be a level that is greater than about 0.30 µM as measured in BM plasma. In some cases, an elevated level of 2-HG can be a level that is greater than about 0.70 µM as measured in PB plasma. In some cases, when control samples have undetectable levels of 2-HG an elevated level can be a detectable level of 2-HG It will be appreciated that levels from comparable samples are used when determining whether or not a particular level is an elevated level.

A oncometabolite can be any metabolite that is associated with a cancer. In some cases, the oncometabolite can be a metabolite derived from glutamine. Examples of metabolites derived from glutamine include, without limitation, 2-HG glutamate, α-ketoglutarate, succinate, fummarate, oxaloacetate, and aspartate. In some cases, an elevated level of 2-HG can be used to identify patients who are at high risk of progressing from a precursor PC disorder (e.g., SMM) to a PC cancer (e.g., MM). In some cases, an elevated level of 2-HG can indicate that a mammal (e.g., a human) has increased c-Myc expression. Oncometabolites can be D enantiomers, L enantiomers, or a combination thereof.

When treating a mammal (e.g., a human) having a precursor PC disorder as described herein, the precursor PC disorder can be any precursor PC disorder. Examples of precursor PC disorders that can be treated as described herein include, without limitation, MGUS, SMM, solitary plasmacytoma of bone, extramedullary plasmacytoma, primary amyloidosis, light chain deposition disease, paraproteinemia, and heavy-chain disease. In some cases, the materials and methods described herein can be used to treat SMM.

When treating a mammal (e.g., a human) having a precursor PC disorder as described herein, the treatment can be effective to slow or prevent the progression to any PC cancer. Examples of PC cancers include, without limitation, MM, Waldenström's macroglobulinemia (WM), plasmacytoma, plasma cell leukemia non-secretory myeloma, and extramedullary myeloma. In some cases, the materials and methods described herein can be used to slow or prevent progression of a precursor PC disorder to MM.

Any type of mammal having a precursor PC disorder can be assessed and/or treated as described herein. In some cases, humans and other primates such as monkeys having a precursor PC disorder can be assessed for risk of progression to a PC cancer as described herein. For example, humans and other primates such as monkeys having a precursor PC disorder can be identified as having an elevated level of an oncometabolite (e.g., 2-HG), can be classified as being at high risk of progressing from a precursor PC disorder (e.g., SMM) to a PD cancer (e.g., MM). In some cases, humans and other primates such as monkeys having a precursor PC disorder likely to progress to a PC cancer can be treated as described herein. For example, humans and other primates such as monkeys classified as being at high risk of progressing from a precursor PC disorder (e.g., SMM) to a PD cancer (e.g., MM) can be treated with one or more PC cancer treatments and/or one or more c-Myc inhibitors as described herein. In some cases, humans and other primates such as monkeys having a precursor PC disorder can be identified as having an elevated level of an oncometabolite (e.g., 2-HG), can be classified as being at high risk of progressing from a precursor PC disorder (e.g., SMM) to a PD cancer (e.g., MM), and can be treated with one or more PC cancer treatments and/or one or more c-Myc inhibitors as described herein. In some cases, dogs, cats, horses, cows, pigs, sheep, rabbits, mice, and rats can be assessed and/or treated as described herein.

Any appropriate method can be used to identify a mammal having precursor PC disorder. For example, imaging techniques, biopsy techniques, blood tests (e.g., M-spike, serum free light chain (FLC) ratio, hemoglobin, total calcium, creatinine, β-2-microglobulin, immunoglobulin subtype quantification, and immunofixation), urine tests (e.g., 24 hour urinary protein electrophoresis and immunofixation), BM PC percentage, and/or genetic tests (e.g., cytogenetics and fluorescent in situ hybridization (FISH)) can be used to identify mammals (e.g., humans) having precursor PC disorder.

Once identified as having precursor PC disorder, the mammal can be assessed to determine whether or not the precursor PC disorder will progress to a PC cancer. For example, a sample (e.g., a biological sample) obtained from the mammal having a precursor PC disorder can be assessed for an elevated level of 2-HG Any appropriate sample from a mammal (e.g., a human) having a precursor PC disorder can be assessed to determine if the mammal has an elevated level of an oncometabolite (e.g., 2-HG). In some cases, biological samples such as tissue samples (e.g., BM, such as BM PCs, or a plasmacytoma), and fluids (e.g., blood, serum, plasma (e.g., BM plasma and peripheral blood (PB) plasma), and urine) can be obtained from a mammal and assessed for the presence of an elevated level of 2-HG For example, BM plasma can be obtained and assessed to determine whether or not the mammal has an elevated level of 2-HG In some cases, PB plasma can be obtained and assessed to determine whether or not the mammal has an elevated level of 2-HG In some cases, tandem MS/MS can also be utilized in combination with GC or LC to determine whether or not a particular sample contains an elevated level of 2-HG.

Any appropriate method can be used to detect the presence, absence, or level of an oncometabolite (e.g., 2-HG) within a sample (e.g., BM plasma or PB plasma). For example, mass spectrometry (MS) techniques (e.g., gas chromatography-MS (GC/MS), and liquid chromatography-MS (LC/MS)), and bioluminescence can be used to determine whether or not a sample contains an elevated level of 2-HG In some cases, GC-MS can be used to determine whether or not a particular sample contains an elevated level of 2-HG GC-MS can be operated under electron impact (EI) conditions. GC-MS can include selected ion monitoring (SIM).

Once identified as having an elevated level of an oncometabolite (e.g., 2-HG), a mammal (e.g., human) having a precursor PC disorder can be classified as being at high risk of progressing from a precursor PC disorder (e.g., SMM) to a PD cancer (e.g., MM). A mammal identified as being at high risk of progressing from a precursor PC disorder (e.g., SMM) to a PD cancer (e.g., MM) can be administered or instructed to self-administer one or more PC cancer (e.g., MM) treatments. Treatments for MM include, without limitation, targeted therapies (such as bortezomib (e.g., Velcade®, Neomib®, and Bortecad), carfilzomib (e.g., Kyprolis®), and ixazomib (Ninlaro®)), biological therapies (such as thalidomide (e.g., Thalomid®), lenalidomide (e.g., Revlimid®), and pomalidomide (e.g., Pomalyst®)), chemotherapies (such as melphalan, vincristine (e.g., Oncovin), cyclophosphamide (e.g., Cytoxan and Neosar), etoposide (e.g., VP-16 and Etopophos), doxorubicin (e.g., Adriamycin, Doxil, Caelyx, and Myocet), and bendamustine (e.g., Treanda®)), corticosteroids (e.g., prednisone and dexamethasone), stem cell transplantation, radiation therapy, antibody therapy (such as daratumumab (Darzalex®) and elotuzumab (Empliciti®)), chimeric antigen receptor T cell therapy, and allogeneic stem cell transplantation.

In some cases, a mammal (e.g., human) identified as having an elevated level of an oncometabolite (e.g., 2-HG) as described herein can be administered or instructed to self-administer one or more c-Myc inhibitors. A c-Myc inhibitor can be an inhibitor of c-Myc polypeptide expression, an inhibitor of c-Myc polypeptide activity, or a c-Myc pathway inhibitor. Examples of molecules in the c-Myc pathway that can be targeted by an inhibitor (e.g., an inhibitor of polypeptide expression or an inhibitor of polypeptide activity) as described herein include, without limitation, glutaminase. For example, a c-Myc pathway inhibitor can be an inhibitor of glutamine metabolism (e.g., a glutaminase inhibitor). Example compounds that reduce c-Myc polypeptide activity include, without limitation, 10058-F4 and analogs and/or derivatives thereof. Example compounds that reduce glutaminase polypeptide activity include, without limitation, CB-839, BPTES, and analogs and/or derivatives thereof. Examples of compounds that reduce c-Myc polypeptide expression include, without limitation, nucleic acid molecules designed to induce RNA interference (e.g., a siRNA molecule or a shRNA molecule), antisense molecules, and miRNAs. In cases wherein a c-Myc inhibitor is an siRNA, the siRNA can include a deoxythymidine dinucleotide (dTdT) overhang. Examples of such siRNA molecules include, without limitation, those set forth in Table 1.

TABLE 1

Examples of siRNA molecules targeting c-Myc.

| Sequence | Species | SEQ ID NO: |
|---|---|---|
| GCCACAGCAUACAUCCUGUUU | Human | 1 |
| GGUCAGAGUCUGGAUCACC | Human | 2 |
| GAUGAGGAAGAAAUCGAUG | Human | 3 |

Additional c-Myc inhibitors can be readily designed based upon the nucleic acid and/or polypeptide sequences of c-Myc and/or molecules in the c-Myc pathway (e.g., glutaminase).

Administration of one or more PC cancer treatments and/or one or more c-Myc inhibitors to a mammal (e.g., human) having an elevated level of 2-HG can be effective to treat a precursor PC disorder (e.g., slow or prevent progression to MM). In some cases, the materials and methods provided herein can be used to slow or prevent the symptoms of MM. Symptoms of MM can include, without limitation, bone pain (e.g., in the spine and/or chest), nausea, constipation, loss of appetite, mental fogginess or confusion, fatigue, frequent infections, weight loss, weakness or numbness in your legs, excessive thirst, and lower extremity edema and/or swelling. In some cases, the materials and methods provided herein can be used to slow or prevent a complication associated with MM. Complications associated with MM can include, without limitation, frequent infections, bone problems (e.g., bone pain, thinning bones, and broken bones, reduced kidney function (e.g., kidney failure), blood problems (e.g., anemia, thrombocytopenia, and neutropenia), and electrolyte abnormalities (e.g. hypercalcemia).

The invention will be further described in the following examples, which do not limit the scope of the invention described in the claims.

EXAMPLES

Example 1: 2-HG in PCs

Methods

Cell Culture Preparation and Isotope Labelling

The MM1S and CCL-155 (RPMI-8226) human myeloma cell lines (HMCLs) were obtained from American Type Culture Collection (ATCC). These HMCLs were grown in RPMI-1640 cell culture medium containing 11 mM of glucose and supplemented with 10% fetal bovine serum (FBS), 2 mM Glutamax (GIBCO, Grand Island, N.Y.), 100 U/mL penicillin, and 100 µg/mL streptomycin. The cell culture incubators were set at 37° C. and 5% $CO_2$/air. For the $^{13}C$-labelling experiments, the HMCLs were eventually re-suspended in media containing $^{13}C$-labelled isotopes when they reached 60-70% confluency. In labelling experiments using $^{13}C$-labelled glucose, 35% of the glucose in the aforementioned cell culture media was substituted with U-$^{13}C_6$-Glucose (Cambridge Isotopes, Mass.) to maintain a stable concentration of 11 mM of glucose. Similarly, in labelling experiments using $^{13}C$-labelled glutamine, 35% of the glutamine in the aforementioned cell culture media was substituted with U-$^{13}C_5$-Glutamine (Cambridge Isotopes, Mass.) to maintain a concentration of 2 mM. All cell lines were passaged less than 5 times between thawing and the completion of U-$^{13}C_6$-Glucose or U-$^{13}C_5$-Glutamine labeling experiments. A sample of the labeling media was taken at the initial time of labelled media preparation and stored as a reference for analysis. Additional samples of the labeling media were collected at 12 and 24 hours. Following the each of the 12 and 24-hour labeling periods, cell pellets of the HMCLs were harvested by rinsing with phosphate-buffered saline three times after centrifugation at 500×g for 6 minutes. These cell pellets were stored at −80° C. for subsequent TCA cycle intermediate isotopomer analyses.

TCA Cycle Intermediates Isotopomer Analysis
Sample Preparations

The HMCL cell pellet extracts were derivatized using 20 µL of a 20 mg/mL ethoxyamine hydrochloride solution in pyridine for 60 minutes at 70° C. Subsequently, the extracts were silylated with 100 µL of MTBSTFA (N-Methyl-N-(tert-butyldimethylsilyl) trifluoroacetamide) and 1% tBDMS (Tertbutyldimetheylchlorosilane) (Regis Technologies, Ill., USA) for 60 minutes at 35° C. followed by overnight incubation at room temperature (Maud et al., 2006). After evaporation to dryness using nitrogen, the residues were redissolved in 25 µL n-decane.

GC/MS Analyses

Isotopomer analysis of the intracellular and extracellular TCA cycle metabolites from the HMCL cell pellets and spent media respectively were per performed using an Agilent Technologies 5975C GC/MS (Agilent Inc, Calif., USA). Splitless injections of 1 µL aliquots of the derivatized extracts were injected onto a DB5-MS capillary column (30 m×250 µm i.d., 0.25 µm film thickness; J&W Scientific, Folson, Calif.). The mass spectrometer was operated under electron impact (EI) conditions with selected ion monitoring (SIM). The temperature of the injector was set at 250° C. and the transfer line to the MS at 280° C. Helium was used as the carrier gas at a flow rate of 0.9 mL/minute. The GC temperature program used was: oven held for 0.5 min at 120° C., then increased to 210° C. at 15° C./minute, then to 270° C. at 10° C./minute, to 280° C. at 5° C./minute holding for 1 minute and finally increased to 325° C. with a hold time of 10 minutes. Data were processed using Agilent Chemstation and MassHunter quantitative analysis software version B.05.01 build 5.1.315.0 (Agilent Technologies Inc., Calif., USA) for integration of peaks and calculation isotopic ratios.

SIM was used to monitor the mole percent enrichment for each analyte, such as the fragment (M0) and all labeled mass isotopomer positions (M1, M2, M3 etc.) up to m+3 above the number of carbons in the molecule backbone. M/z values of M0 were monitored for the following intermediates: lactate (m/z 261.2), fumarate (m/z 287.1), succinate (m/z 289.1), α-ketoglutarate (m/z 360.2), malate (m/z 419.3), citrate (m/z 591.4), 2-HG (m/z 363.2) and glutamate (m/z 432.2). The mass isotopomer distribution of each compound was then corrected for natural abundance using the respective standards. An appropriate set of linear simultaneous equations was used to calculate mole percent enrichment of TCA cycle intermediates to understand glucose dependent or glucose independent glutamine metabolism in myeloma cells.

siRNA Knockdown of c-Myc and GLS1

The MM1S cells were nucleofected with 1.5 µM of c-Myc siRNAs using the Amaxa Nucleofection kit (Lonza, Basel, Switzerland) (kit V, protocol O23) and following the manufacturers protocol. At 36 hours post transfection, the cells were re-suspended in RPMI1640 media containing 100% $^{13}C$ glutamine and supplemented with 10% FBS, 100 U/mL penicillin, and 100 µg/mL streptomycin (0.3 mg/ml (CLM-1822-H-0.1, Cambridge isotope). The cells were harvested 12 hours later for 2-HG isotopomer assessments.

Statistical Analysis

Fractional abundance of $^{13}C$ in the various TCA metabolites is expressed as mean±standard deviation (SD). Data were compared and analyzed using the Student's t test, and significance was defined as $p<0.05$.

Results

Assessment of Glucose and Glutamine Utilization for the TCA Cycle Flux in HMCLs

The HMCLs, MM1S and RPMI-8226, were utilized to assess the incorporation of glucose and glutamine into the TCA cycle by incubating them in cell culture media containing 35% U-$^{13}C_6$-Glucose and 35% U-$^{13}C_5$-Glutamine respectively. Both cell lines are known to have c-Myc overexpression based on gene expression profiling of the various HMCLs. The incorporation of labelled U-$^{13}C_6$-Glucose and U-$^{13}C_5$-Glutamine into the various intracellular TCA cycle substrates is shown in both HMCLs at 12 hours (FIG. 1A). With the first turn of the TCA cycle, U-$^{13}C_6$-Glucose-derived TCA cycle intermediates would be expected to yield (m+2) isotopomers of citrate, α-ketoglutarate, glutamate, succinate, malate and aspartate. Whereas U-$^{13}C_5$-Glutamine-derived TCA cycle intermediates would be expected to yield (m+5) isotopomers of α-ketoglutarate and glutamate but (m+4) isotopomers of succinate, malate, aspartate and citrate. The formation of (m+5) citrate in MM1S cells incubated in U-$^{13}C_5$-Glutamine reflects the reductive carboxylative activity present in which citrate is formed from α-ketoglutarate, albeit it accounts for only a small percentage of the $^{13}C$ derived from glutamine anaplerosis. The dilution of the intracellular unlabeled TCA intermediate pool (i.e., m+0 TCA intermediates) with their corresponding $^{13}C$ isotopomers is much higher in HMCLs incubated with U-$^{13}C_5$-Glutamine than U-$^{13}C_6$-Glucose which suggests a higher percentage incorporation of glutamine into the TCA cycle via anaplerosis compared to glucose entry into the TCA cycle via pyruvate. Overall, these results confirmed the role of glutamine as an important carbon source by providing an appreciable anaplerotic flux into the TCA cycle.

Figure 1B:
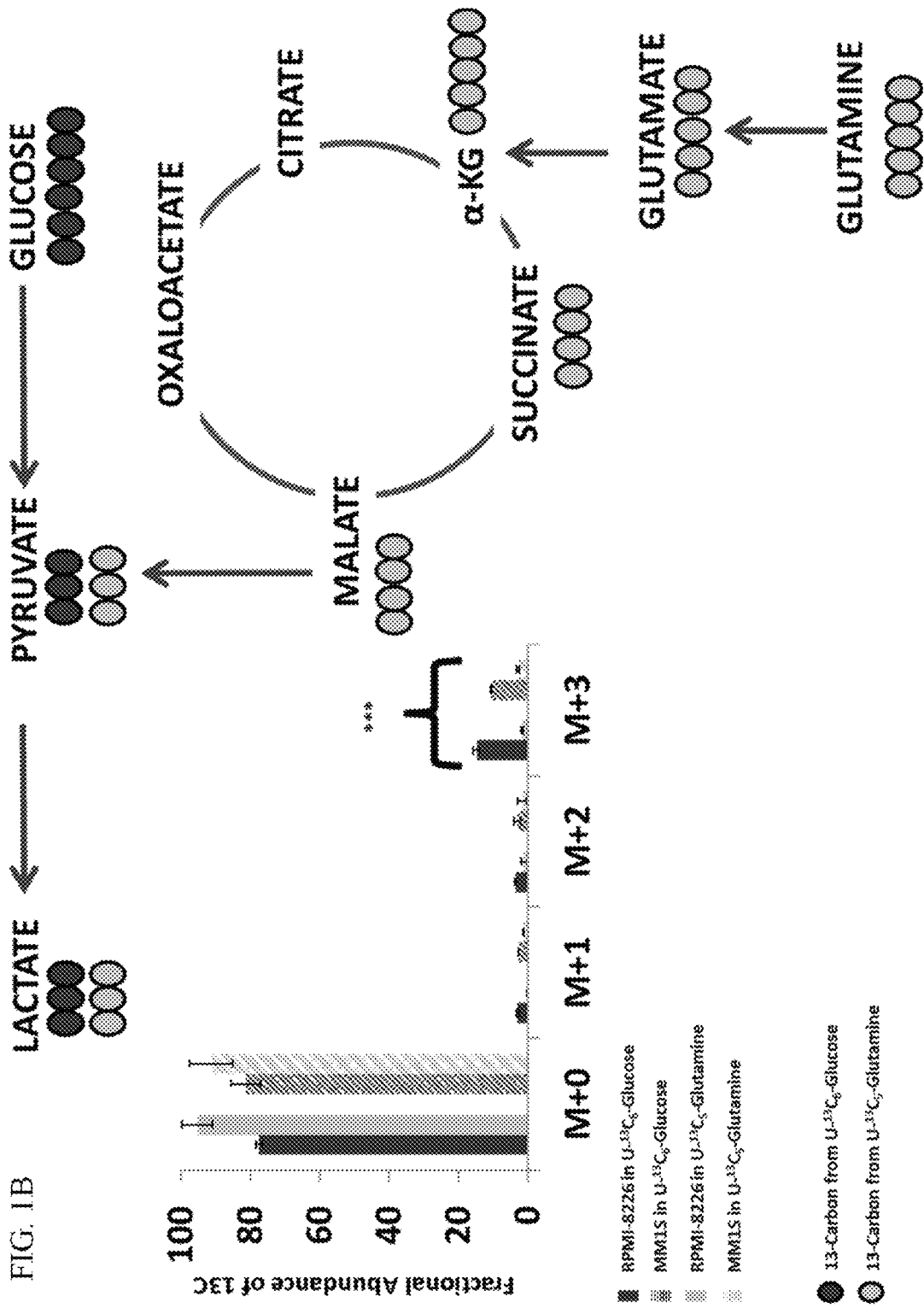
FIG. 1B is a mass isotopomer distribution of lactate after incubation of MM1S or RPMI-8226 HMCLs in cell culture media containing either U-$^{13}C_5$-Glutamine or U-$^{13}C_6$-Glucose. The (m+3) isotopomers highlighted in lighter grey and darker grey circles represent the isotopomer derived from U-$^{13}C_5$-Glutamine and U-$^{13}C_6$-Glucose respectively.

Assessment of Glucose and Glutamine Utilization for the Aerobic Glycolysis Flux in HMCLs Similarly, the HMCLs, MM1S and RPMI-8226, were utilized to assess the incorporation of glucose and glutamine into the aerobic glycolysis pathway by using cell culture media containing 35% U-$^{13}C_6$-Glucose and 35% U-$^{13}C_5$-Glutamine respectively. The incorporation of labelled U-$^{13}C_6$-Glucose and U-$^{13}C_5$-Glutamine into intracellular lactate was evaluated in both HMCLs at 12 hours. U-$^{13}C_6$-Glucose would be expected to yield (m+3) isotopomers of lactate through the formation of (m+3) pyruvate. However, U-$^{13}C_5$-Glutamine would be expected to also yield an (m+3) isotopomer of lactate as a result of (m+4) malate conversion to (m+3) pyruvate. The percentage incorporation of $^{13}C$ from U-$^{13}C_6$-Glucose into the (m+3) lactate via aerobic glycolysis is much higher compared to that from U-$^{13}C_5$-Glutamine (P<0.001) (FIG. 1B). These observations are consistent with the Warburg effect being derived entirely from glucose rather than glutamine.

Figure 2A:
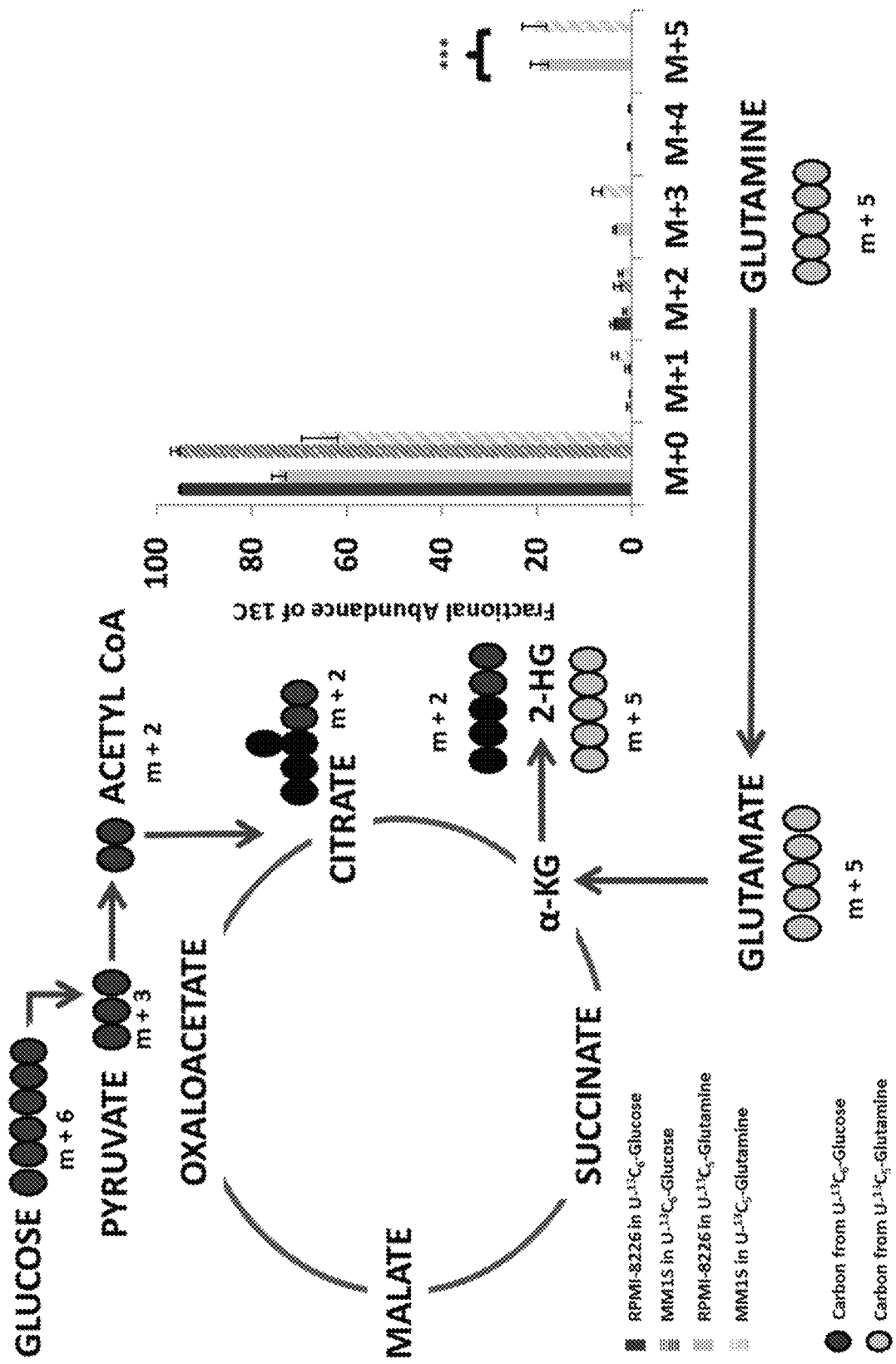
FIG. 2A is a mass isotopomer distribution of 2-HG after incubation of MM1S or RPMI-8226 HMCLs in cell culture media containing either U-$^{13}C_5$-Glutamine or U-$^{13}C_6$-Glucose. The (m+5) isotopomers highlighted in lighter grey circles represent the isotopomer derived from U-$^{13}C_5$-Glutamine and the (m+2) isotopomers highlighted in darker grey circles are derived from U-$^{13}C_6$-Glucose.

Assessment of Glucose and Glutamine Utilization for the Formation of 2-HG in HMCLs Similarly, the HMCLs, MM1S and RPMI-8226, were utilized to assess the incorporation of glucose and glutamine into the formation of 2-HG using cell culture media containing 35% U-$^{13}C_6$-Glucose and 35% U-$^{13}C_5$-Glutamine respectively. The incorporation of labelled U-$^{13}C_6$-Glucose and U-$^{13}C_5$-Glutamine into intracellular 2-HG formation was evaluated in both HMCLs at 12 hours. U-$^{13}C_6$-Glucose would be expected to yield (m+2) isotopomers of 2-HG through the formation of (m+2) α-ketoglutarate. However, U-$^{13}C_5$-Glutamine would be expected to yield an (m+5) isotopomer of 2-HG as a result of (m+5) glutamate conversion to (m+5) α-ketoglutarate. The percentage incorporation of $^{13}C$ from U-$^{13}C_5$-Glutamine into the (m+5) 2-HG is much higher compared to $^{13}C$ from U-$^{13}C_6$-Glucose (P<0.001) (FIG. 2A). This demonstrates that 2-HG is present and formed in clonal PCs and that almost all of the 2-HG appears to be derived from carbon substrates obtained from glutamine anaplerosis into the TCA cycle.

Figure 2B:
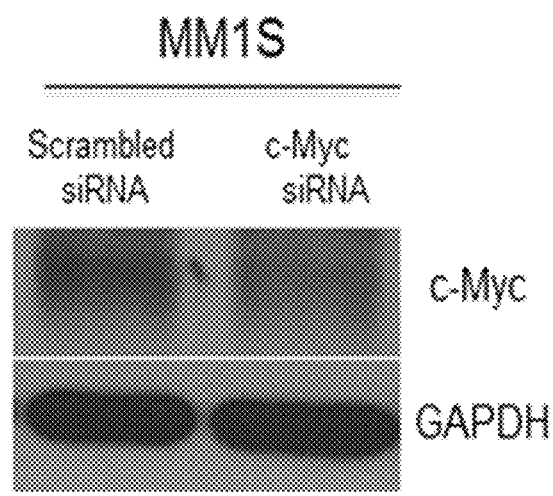
FIG. 2B is a western blot showing knockdown of c-Myc protein expression in MINDS HMCLs via siRNA nucleofection.
Figure 2C:
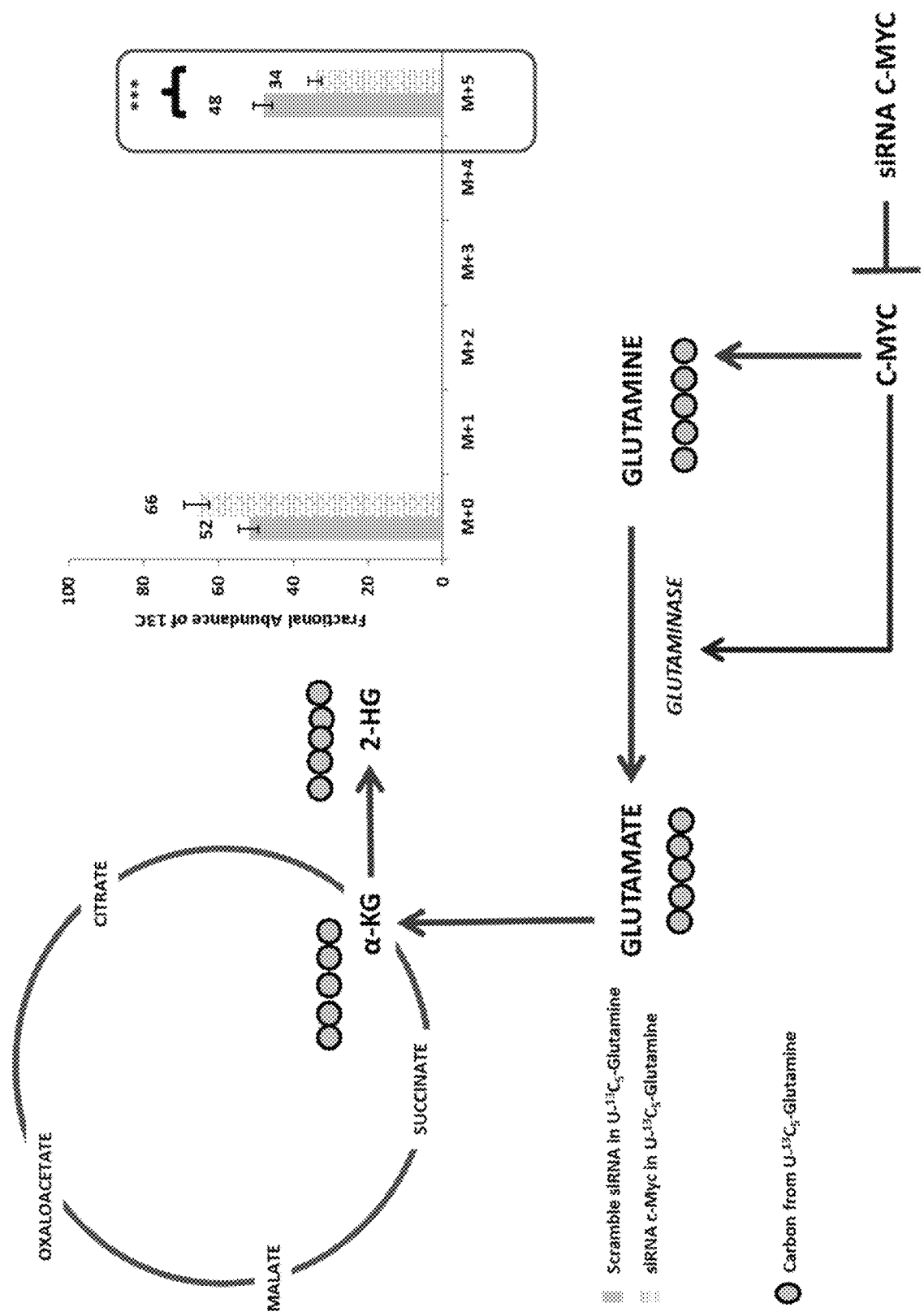
FIG. 2C is a mass isotopomer distribution of 2-HG after incubation of MM1S HMCLs treated with c-Myc siRNA or scramble siRNA in cell culture media containing U-$^{13}C_5$-Glutamine. The (m+5) isotopomers highlighted in the lighter grey circles represents the 2-HG isotopomer derived from U-$^{13}C_5$-Glutamine.

2-HG in MM is Derived Primarily from c-Myc Driven Glutamine Anaplerosis into the TCA Cycle The MM1S HMCLs underwent transient siRNA knockdown of c-Myc (FIG. 2B). The siRNA knockdown HMCLs in addition to scramble siRNA controls were subsequently incubated in cell culture media containing 2 mM of U-$^{13}C_5$-Glutamine. It would be expected as previously described that the U-$^{13}C_5$-Glutamine would yield an (m+5) isotopomer of 2-HG as a result of U-$^{13}C_5$-Glutamine-derived (m+5) glutamate conversion to (m+5) α-ketoglutarate via (m+5) glutamate. The MM1 S cells with c-Myc siRNA show significantly lower proportions of intracellular (m+5) 2-HG compared to the scramble siRNA controls (FIG. 2C). This experiment suggests that the 2-HG formation is dependent on the activity of c-Myc driven glutamine anaplerosis into the TCA cycle.

Assessment of Extracellular Flux of TCA Metabolites in HMCLs

Figure 2D:
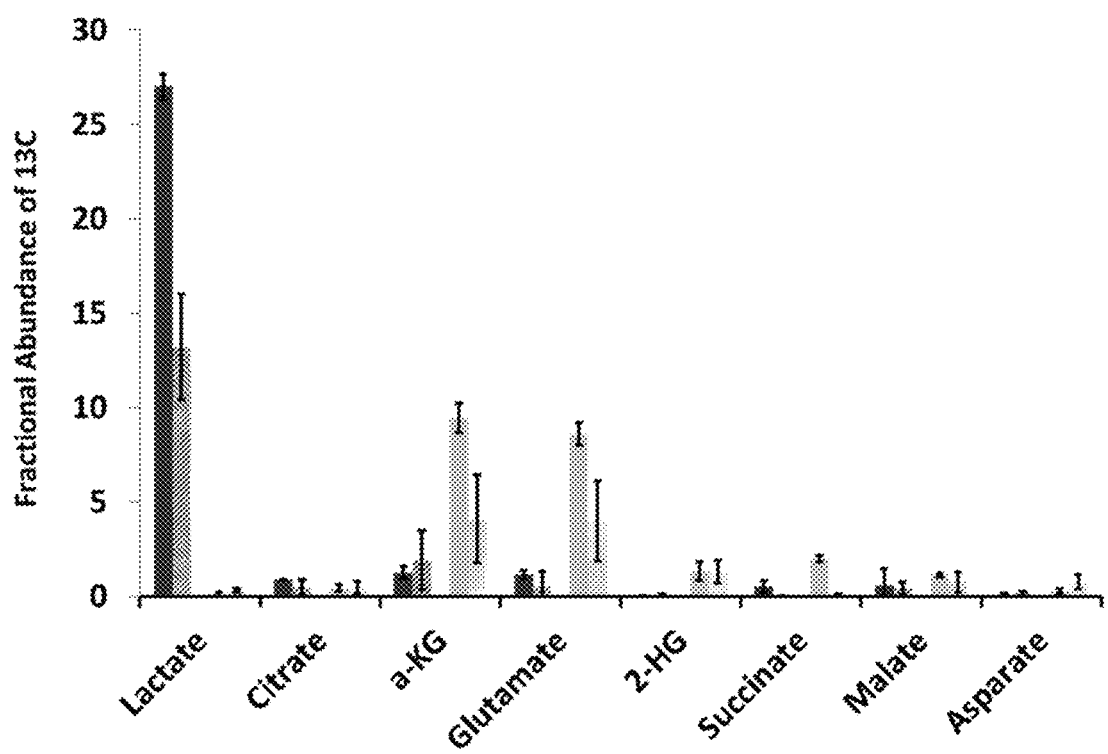
FIG. 2D is a mass isotopomer distribution of the various isotopomers present in the spent media of HMCLs after 24 hours of incubation.

In order to determine whether any of the TCA metabolites formed intracellularly in the HMCLs is released extracellularly, the spent media of the HMCLs incubated for 24 hours in cell culture media containing 35% U-$^{13}C_6$-Glucose and 35% U-$^{13}C_5$-Glutamine were evaluated by GC-MS for $^{13}C$ isotopomers and shown in FIG. 2D. Particular TCA metabolites were found to be released extracellularly in relatively large quantities such as lactate, glutamate, α-ketoglutarate and 2-HG compared to the remainder of metabolites. Most of the secreted lactate produced from aerobic glycolysis was derived from glucose instead of glutamine as seen by the high levels of (m+3) lactate. The remainder of the secreted TCA metabolites are produced from glutamine instead of glucose as demonstrated by the high levels of (m+5) glutamate, α-ketoglutarate and 2-HG as well as (m+4) citrate, succinate, malate and aspartate.

Example 2: 2-HG is Associated with Disease Progression in SMM

Methods

Ex Vivo $^{13}C$ Labelling of CD138+ and CD138-Mononuclear Cells

The freshly obtained BM aspirates from patient underwent Ficoll-Paque gradient separation for plasma processing which was stored for later analysis at −80° C. The remnant cellular component of the BM aspirate underwent red cell lysis using ACK lysis buffer. The clonal PCs were extracted using positive selection by mixing the cells with a CD138 positive selection cocktail and anti-CD138 magnetic-activated cell separation microbeads (ROBOSEP™ cell separation system, StemCell Technologies Inc.) in an automated RoboSep cell separation system. Purity of the sorted clonal PCs was confirmed via light chain restriction using slide-based immunofluorescent method. The CD138+ clonal PCs and the remainder of the CD138− cells were incubated in RPMI-1640 medium containing 11 mM of glucose and supplemented with 10% fetal bovine serum (FBS), 2 mM U-$^{13}C_5$-Glutamine, 100 U/mL penicillin and 100 μg/mL streptomycin.

Methodology for Quantitative Assessments of TCA Metabolites Via GC MS:

Spent media and plasma samples were spiked in 20 μl of internal solution containing U-$^{13}C$ labeled analytes. The proteins were removed by adding 250 μl of chilled methanol and acetonitrile solution to the sample mixture. After drying the supernatant in the speed vac, the sample was derivatized with ethoxime and then with MtBSTFA+1% tBDMCS before it was analyzed on an Agilent 5975C GC/MS under electron impact and single ion monitoring conditions. Concentrations of lactate (m/z 261.2), succinate (m/z 289.1), oxaloacetate (m/z 346.2), α-ketoglutarate (m/z 360.2), malate (m/z 419.3), citrate (m/z 591.4), 2-HG (m/z 363.2), and glutamate (m/z 432.4) were measured against a 7-point calibration curves that underwent the same derivatization.

Clinical Assessment of Patients with PC Disorders

MGUS and MM:

Consecutive patients with MM and MGUS who underwent q BM aspiration were prospectively evaluated as part of their clinical evaluation. The diagnostic criteria of the International Myeloma Working Group (IMWG) were applied to confirm the diagnosis of MGUS and MM. Their BM plasma was extracted from the BM aspirate and stored in EDTA tubes at −80° C. These later underwent quantification of their TCA metabolite concentrations via GC-MS.

SMM:

Patients with a known diagnosis of SMM and already had their PB or BM plasma stored in the biobank were also evaluated. The diagnostic criteria of IMWG were applied to confirm the diagnosis of SMM: presence of a serum monoclonal immunoglobulin level ≥3 g/dl, and/or BM infiltration with monotypic PCs equal or exceeding 10%, in the absence of end-organ damage attributable to the plasma cell disorder.

For all MGUS, SMM, or MM patients whose PB or BM plasma samples were evaluated for TCA metabolite concentration quantification, their relevant laboratory data, including M-spike, serum free light chain (FLC) ratio, hemoglobin, total calcium, creatinine, β-2-microglobulin, Immunoglobulin subtype quantification, 24 hour urinary protein electrophoresis and immunofixation, BM PC percentage, cytogenetics and fluorescent in situ hybridization (FISH) results were abstracted for analysis.

Statistical Analysis

TTP analysis was done using the Kaplan-Meier method. Differences between TTP curves were tested for statistical significance using the two-sided log-rank test unless otherwise specified.

Results

Figure 3A:
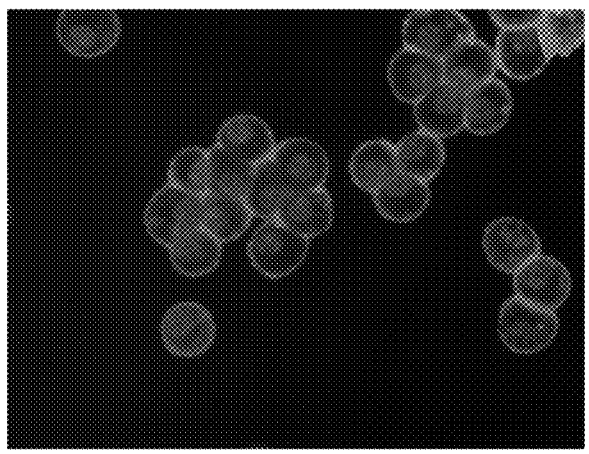
FIG. 3A is a photograph of the light chain restriction of plasma cells to confirm clonality. Staining of the membranes represents kappa restriction and staining that represents lambda restriction is absent.
Figure 3B:
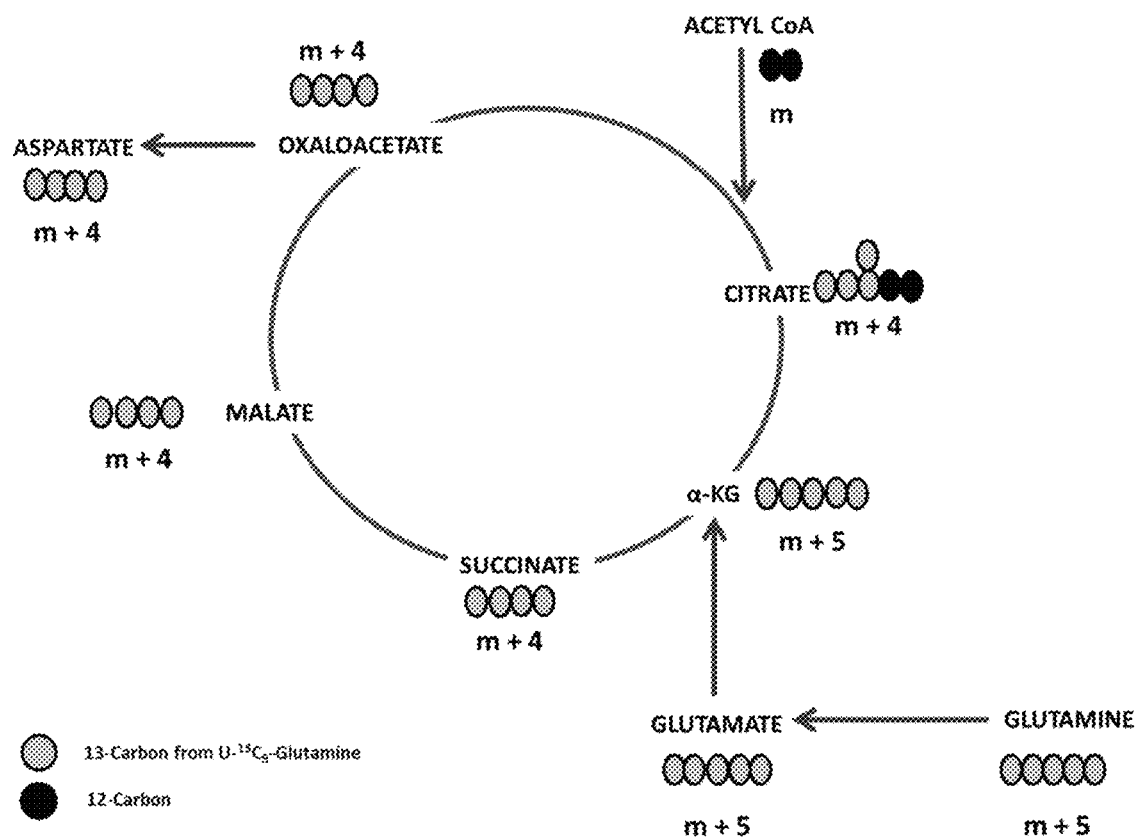
FIG. 3B is a mass isotopomer distribution of the intermediates in the TCA cycle as a result of glutamine anaplerosis of U-$^{13}C_5$-Glutamine. Each intermediate is represented by the number of carbon atoms in their molecular structure with lighter grey circle representing $^{13}C$ and black circles representing $^{12}C$.
Figure 3C:
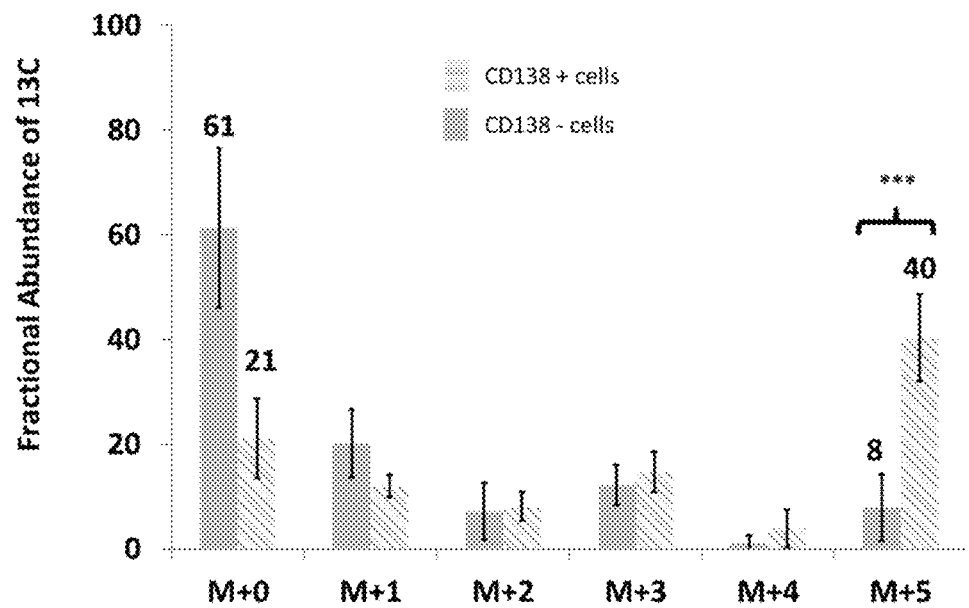
FIG. 3C is a mass isotopomer distribution of glutamate representing the results of ex vivo glutamine anaplerosis of U-$^{13}C_5$-Glutamine into CD138 positive and CD138 negative cells derived from the bone marrow aspirates of patients with MM.
Figure 3D:
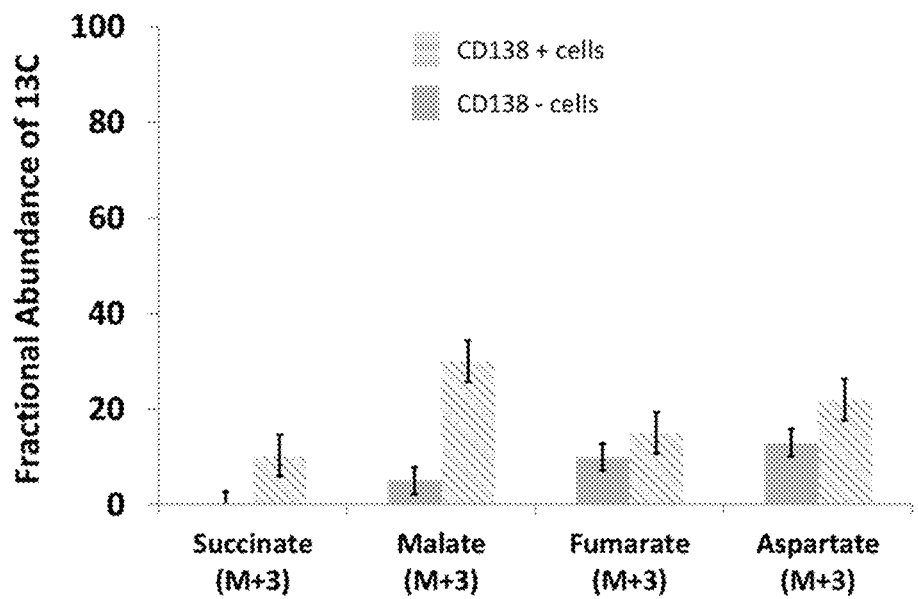
FIG. 3D is a mass isotopomer distribution of the various TCA cycle intermediates as a result of ex vivo glutamine anaplerosis of U-$^{13}C_5$-Glutamine into CD138 positive and CD138 negative cells derived from the bone marrow aspirates of one of the patients with MM.

BM Clonal Plasma Cells in Multiple Myeloma have Higher Glutamine Uptake Compared to the Remainder of BM Mononuclear Cells Fresh BM aspirates were obtained from four consecutive patients (Table 2) diagnosed with MM and was processed to separate the clonal PCs from the remainder of the BM mononuclear cells based on CD138 expression. The CD138 (+) cells consisted of clonal plasma cells (clonality was confirmed by immunofluorescent slide based kappa or lambda restriction as seen in FIG. 3A) and the CD138 (−) represented the non-plasma cells or remainder of the BM mononuclear cells within the BM microenvironment. Both groups of cells from each patient underwent ex vivo assessment of their glutamine utilization by measuring the mass isotopomer distribution of intracellular glutamate after incubating them in cell culture media containing 2 mM of U-$^{13}C_5$-Glutamine. The expected incorporation of carbon substrate from glutamine into the TCA cycle by anaplerosis is depicted in FIG. 3B. The incorporation of glutamine into the cells was higher in the CD138 (+) fraction of cells compared to the CD138 (−) cells as demonstrated by the higher (m+5) glutamate (P<0.001) detected in the intracellular metabolites by GC-MS (FIG. 3C). The $^{13}C$ also incorporated into the various other intracellular TCA cycle substrates in CD138 (+) cells as a result of the glutamine anaplerosis pathway (FIG. 3D).

TABLE 2

Clinical characteristics of 4 patients with newly diagnosed or relapsed MM

| Clinical Characteristics | Patient #1 | Patient #2 | Patient #3 | Patient #4 |
|---|---|---|---|---|
| Stage of Disease | Relapsed | Relapsed | Newly Dx | Newly Dx |
| Age | 70 | 71 | 64 | 55 |
| Gender | Female | Male | Male | Female |
| BMPCs | 95% | 10% | 40% | 80% |
| FISH | Del 17p, t(4; 14), +1q | Del 17p | Trisomies | +1q |
| S-Phase | 0.7% | 5.1% | 1.2% | 0.8% |
| Paraprotein Type | IgA Kappa | Kappa only | IgG Kappa | IgA Lambda |
| Hgb | 8.1 g/dL | 13.3 g/dL | 13.0 g/dL | 10.7 g/dL |
| Calcium | 9.8 mg/dL | 9.1 mg/dL | 9.3 mg/dL | 10.2 mg/dL |
| Creatinine | 0.9 mg/dL | 1.5 mg/dL | 1.1 mg/dL | 0.8 mg/dL |

Figure 4A:
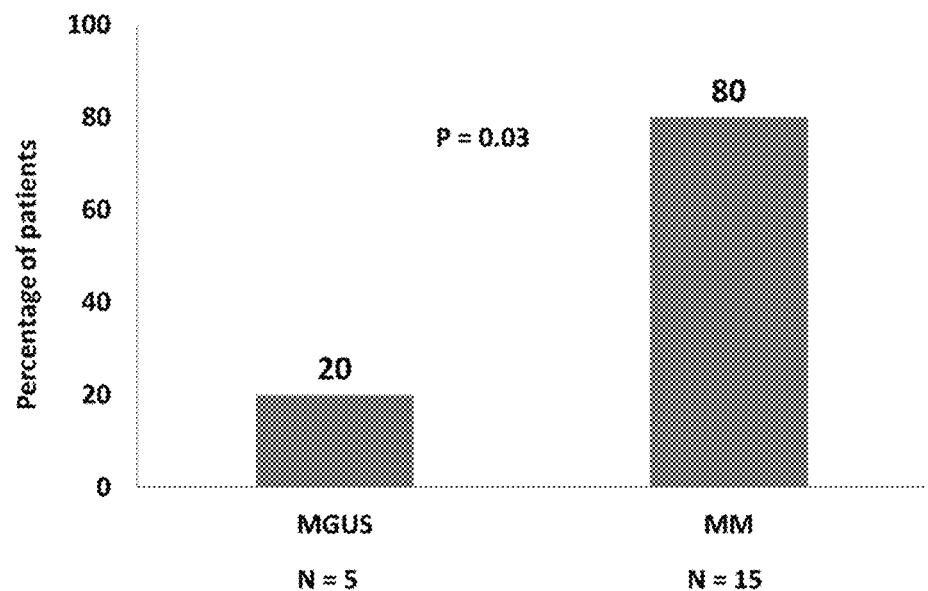
FIG. 4A is a bar graph representing the percentage of MGUS and MM patients with 2-HG levels in the bone marrow plasma higher than the median 2-HG level of the cohort.

Quantification of the TCA Cycle Metabolite Concentrations in BM Plasma of Patients with MGUS and MM A total of 15 consecutive patients with a diagnosis of MM and 5 consecutive patients with a diagnosis of MGUS who were undergoing BM aspirations as part of their routine clinical evaluation provided signed informed consent to allow portions of their BM samples to be utilized for research purposes. Their clinical characteristics as well as the quantification of the various TCA metabolites concentrations in their BM plasma by GC-MS are listed in Table 3. The median concentration of 2-HG measured in the BM plasma was 0.3 µM. Comparative assessments of the 2-HG concentrations between the two groups of MM and MGUS patients demonstrated a higher proportion of MM patients (12/15 patients or 80%) having 2-HG levels more than the median concentration compared to MGUS patients (⅕ patients or 20%) (P=0.03) (FIG. 4A). This supports the fact that since clonal PCs in MGUS lack c-Myc overexpression, they are less likely to produce higher levels of 2-HG that can be released into the BM plasma compared to clonal PCs in MM which are more likely to have c-Myc overexpression producing higher levels of 2-HG.

TABLE 3

Clinical characteristics of patients with MGUS and MM whose BM plasma underwent assessment of TCA metabolite concentrations

| | Age | Gender | BMPC | FISH | S-phase | Paraprotein | Glutamine | 2-HG | a-KG |
|---|---|---|---|---|---|---|---|---|---|
| MGUS #1 | 75 | M | 5 | N/A | 0.3 | IgG lambda | 50 | 0.2 | 12 |
| MGUS #2 | 44 | M | 0 | N/A | N/A | IgG lambda | 91 | 0.2 | 8 |
| MGUS #3 | 73 | F | 5 | N/A | 0.4 | Kappa | 30 | 0.7 | 19 |
| MGUS #4 | 53 | F | 0 | N/A | N/A | IgM lambda | 105 | 0.2 | 11 |
| MGUS #5 | 63 | F | 5 | t(11; 14) | 0.2 | Lambda | 60 | 0.2 | 12 |
| MM #1 | 53 | M | 5 | t(14; 20), +1q | 2.0 | IgA Kappa | 96 | 0.4 | 8.1 |
| MM #2 | 89 | F | 60 | Trisomies | 0.3 | IgG Kappa | 104 | 0.4 | 9.8 |
| MM #3 | 70 | M | 10 | t(4; 14), +1q | N/A | IgA Kappa | 62 | 0.5 | 5.1 |
| MM #4 | 71 | M | 20 | Trisomies | 1.6 | IgG Kappa | 115 | 0.3 | 13 |
| MM #5 | 52 | M | 15 | Trisomies | 0.5 | IgG Kappa | 73 | 0.3 | 8.2 |
| MM #6 | 69 | F | <5 | N/A | N/A | IgA Lambda | 55 | 0.2 | 15.3 |
| MM #7 | 86 | M | 10 | Trisomies | 0.8 | IgG Kappa | 27 | 0.2 | 7.8 |
| MM #8 | 48 | M | 15 | Del17p, Trisomies | 0.9 | IgG Kappa | 68 | 0.5 | 9.2 |
| MM #9 | 78 | M | 10 | N/A | N/A | IgG Kappa | 21 | 0.3 | 6.2 |
| MM#10 | 52 | M | 40 | Trisomies | 1.9 | IgG Kappa | 119 | 0.3 | 7.8 |
| MM#11 | 70 | M | 25 | Del17p, Trisomies | 0.8 | IgG Kappa | 47 | 0.3 | 8.3 |
| MM#12 | 70 | F | 95 | Del17p | 0.7 | IgA Kappa | 81 | 0.3 | 8.2 |
| MM#13 | 74 | F | 40 | +1q, MYC separation | 1.8 | IgG Kappa | 87 | 1.2 | 12.4 |
| MM#14 | 78 | M | 50 | t(11; 14) | 0.3 | IgG Kappa | 60 | 0.5 | 6.9 |
| MM#15 | 77 | M | 95 | Del17p, Trisomies | 2.5 | IgG Kappa | 128 | 0.2 | 11.6 |

Figure 4B:
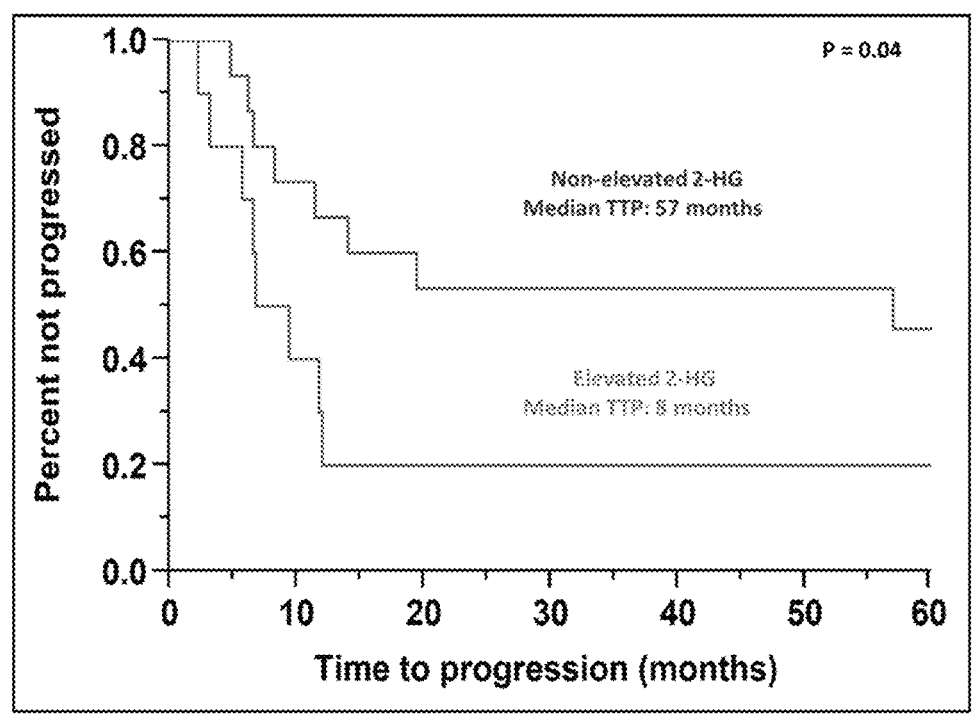
FIG. 4B is a Kaplan-Meir curve comparing the TTP of patients with SMM with a 2-HG level in the bone marrow plasma higher than the median 2-HG level (Elevated 2-HG) to patients with SMM with a 2-HG level in the bone marrow plasma lower or equal to the median 2-HG levels of the cohort (Non-elevated 2-HG).
Figure 4C:
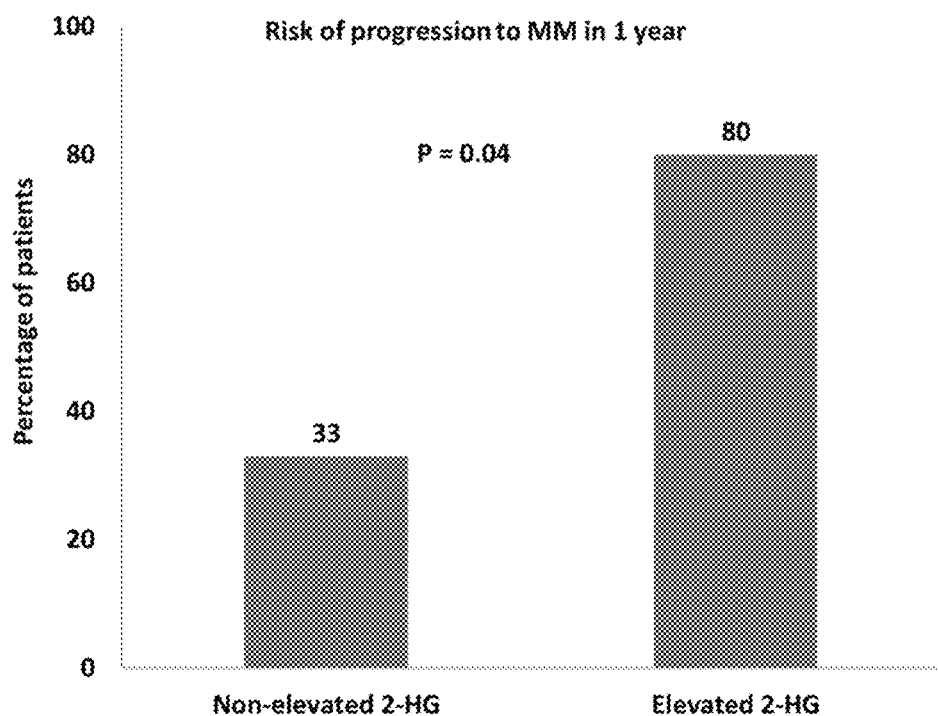
FIG. 4C is a bar graph representing the percentage of SMM patients with 2-HG levels in the bone marrow plasma higher than the median 2-HG level (Elevated 2-HG) or lower than the median 2-HG level (Non-elevated 2-HG) who progressed to MM in one year from the time of 2-HG level assessment.

2-HG Levels Identifies Patients with Smoldering Multiple Myeloma at High Risk of Progression to Multiple Myeloma 25 patients with a diagnosis of SMM were identified who had their initial diagnostic BM plasma samples stored for biobanking purposes. The BM plasma from each of these patients underwent identification and quantification of the various TCA metabolites by GC-MS. The resulting concentrations and clinical characteristics of these patients are listed in Table 4. Increasing levels of 2-HG predicted for a shorter TTP to MM (HR: 2.29, 95% CI: 1.14-4.43; P=0.023). The median 2-HG concentration was 0.30 μM (Range: 0.2-4.2). Patients whose BM plasma 2-HG concentration was above the median was categorized as "elevated 2-HG" (N=10) and those below the median was categorized as "non-elevated 2-HG" (N=15). The non-elevated 2-HG group had a median TTP of 57 months vs. 8 months in the elevated 2-HG group (P=0.04) (FIG. 4B). Also, 80% of SMM patients in the elevated 2-HG group progressed to MM within 1 year vs. 33% of SMM patients in the non-elevated 2-HG group (P=0.04) (FIG. 4C).

TABLE 4

Clinical characteristics of patients with SMM whose BM plasma underwent assessment of TCA metabolite concentrations

| | Age | Gender | BMPC % | FISH | S-phase | Glutamine | 2-HG | a-KG |
|---|---|---|---|---|---|---|---|---|
| SMM#1 | 55 | F | 50% | t(11; 14) | 0.3 | 28 | 0.4 | 5.5 |
| SMM#2 | 68 | F | 15% | trisomies | 2 | 70 | 0.5 | 8.4 |
| SMM#3 | 64 | M | 25% | N/A | | 127 | 1.4 | 6.1 |
| SMM#4 | 66 | M | 30% | Del 13 | 0 | 199 | 1.7 | 9.3 |
| SMM#5 | 57 | M | 15% | trisomies | 0 | 64 | 0.2 | 7.7 |
| SMM#6 | 66 | M | 50% | N/A | 1.4 | 58 | 0.5 | 6.6 |
| SMM#7 | 67 | F | 15% | del13, t(4; 14) | 1 | 86 | 0.6 | 9.6 |
| SMM#8 | 66 | M | 40% | del 17p, trisomies | 0.9 | 61 | 0.5 | 7.0 |
| SMM#9 | 82 | M | 30% | trisomy 3, 7, 9, 11, 15 | 1 | 32 | 0.3 | 6.7 |
| SMM#10 | 72 | F | 20% | del13, del14 | | 48 | 0.3 | 8.4 |
| SMM#11 | 54 | F | 15% | N/A | 0 | 403 | 0.2 | 0.3 |
| SMM#12 | 79 | M | 50% | t(11; 14), +3, trans14 | 2 | 42 | 4.2 | 6.9 |
| SMM#13 | 60 | F | 20% | del13, t(4; 14) | 0.4 | 31 | 0.3 | 7.0 |
| SMM#14 | 67 | F | 40% | N/A | 0.4 | 195 | 0.3 | 0.6 |
| SMM#15 | 80 | F | 50% | t(11; 14) | 0.2 | 37 | 0.2 | 5.5 |
| SMM#16 | 61 | M | 15% | t(4; 14) | 0.2 | 36 | 0.4 | 6.3 |
| SMM#17 | 62 | F | 30% | IgH rearrangement | 0 | 76 | 0.3 | 7.2 |
| SMM#18 | 42 | M | 10% | del 13, t(6; 14) | 0.4 | 61 | 0.2 | 4.9 |
| SMM#19 | 61 | M | 15% | trisomy 7, 9, 11, struc 17 | 0.1 | 42 | 0.3 | 5.0 |
| SMM#20 | 60 | F | 10% | N/A | 0 | 74 | 0.3 | 8.0 |
| SMM#21 | 71 | M | 10% | trisomy 3, 7, 9, 15 | 0 | 39 | 0.3 | 5.7 |
| SMM#22 | 64 | F | 30% | Monosomy 13, Trisomy 3 | 0 | 158 | 0.3 | 5.6 |
| SMM#23 | 30 | F | 30% | del 13, 14 rearranged, trisomy 11 | 0.2 | 299 | 0.6 | 3.3 |

TABLE 4-continued

Clinical characteristics of patients with SMM whose BM plasma underwent assessment of TCA metabolite concentrations

|        | Age | Gender | BMPC % | FISH                        | S-phase | Glutamine | 2-HG | a-KG |
|--------|-----|--------|--------|-----------------------------|---------|-----------|------|------|
| SMM#24 | 57  | M      | 10%    | Del13, trisomy 3, 7, 9, 11, 15 | 0       | 243       | 0.3  | 11.6 |
| SMM#25 | 38  | M      | 20%    | N/A                         | 0       | 133       | 0.2  | 4.4  |

Figure 4D:
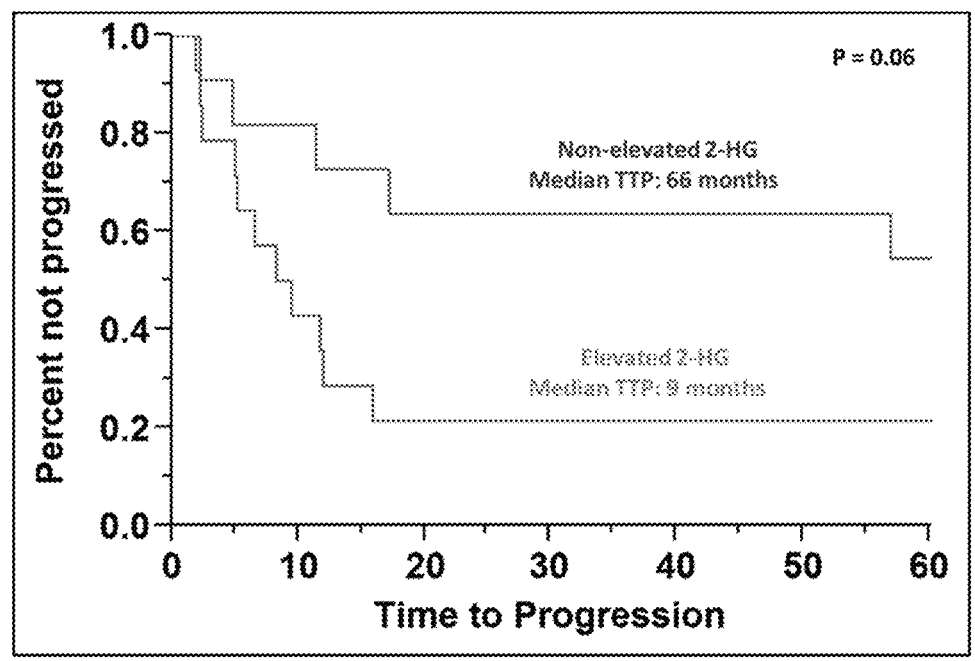
FIG. 4D is a Kaplan-Meir curve comparing the TTP of patients with SMM with a 2-HG level in the peripheral blood plasma higher than the median 2-HG level (Elevated 2-HG) to patients with SMM with a 2-HG level in the peripheral blood plasma lower or equal to the median 2-HG levels of the cohort (Non-elevated 2-HG)
Figure 4E:
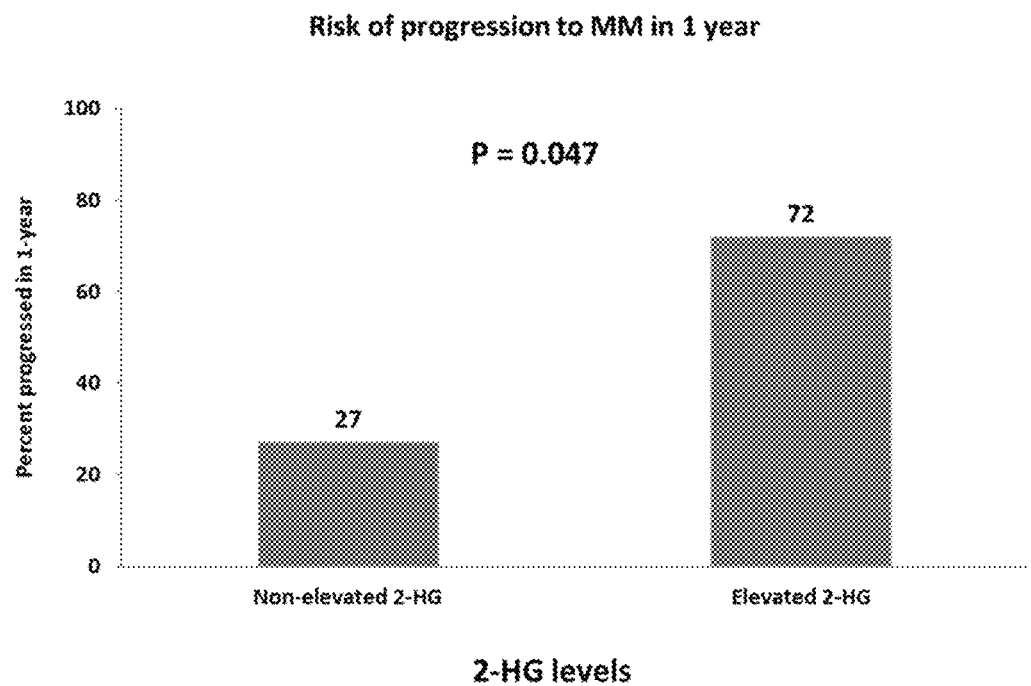
FIG. 4E is a bar graph representing the percentage of SMM patients with 2-HG levels in the peripheral blood plasma higher than the median 2-HG level (Elevated 2-HG) or lower than the median 2-HG level (Non-elevated 2-HG) who progressed to MM in one year from the time of 2-HG level assessment.

To verify whether these differences in 2-HG concentrations were reproducible, similar TCA metabolite quantifications were performed in the PB plasma of 25 patients with SMM. The clinical characteristics and resulting concentrations of these patients are listed in Table 5. Just as in the BM plasma, increasing levels of 2-HG in the PB plasma predicted for a shorter TTP to MM (HR: 2.89, 95% CI: 1.13-9.8; P=0.029). The median 2-HG concentration was 0.70 μM (Range: 0.37-4.63). Patients whose PB plasma 2-HG concentration was above the median were categorized as "elevated 2-HG" (N=14) and those below the median were categorized as "non-elevated 2-HG" (N=11). The non-elevated 2-HG group had a median TTP of 66 months vs. 9 months in the elevated 2-HG group (P=0.06) (FIG. 4D). Also, 72% of SMM patients in the elevated 2-HG group progressed to MM within 1 year vs. 27% of SMM patients in the non-elevated 2-HG group (P=0.047) (FIG. 4E). This data supports the fact that patients with SMM who progress rapidly to MM are likely to have elevated 2-HG levels in their PB or BM plasma given that their clonal PCs are similar to clonal PCs in MM that are characterized by c-Myc overexpression. Whereas patients with SMM who do not progress to MM over a very long time are likely to have non-elevated 2-HG levels in their PB or BM plasma since their clonal PCs are similar to those in MGUS that lack c-Myc overexpression.

These results demonstrate that elevated levels of 2-HG in in precursor PC disorders such as SMM and MGUS can be used to identify patients at high risk of progression to MM.

Example 3: 2-HG is Associated with c-Myc Expression in PCs

Methods

Immunohistochemistry (IHC)

The c-MYC IHC stain was carried out using the Biocare MACH 3 Detection system. A 4-μm tissue section was cut from the BM core biopsy paraffin block and mounted on a charged slide, which was then deparaffinized and hydrated. Endogenous peroxidase was blocked using hydrogen peroxide. Heat-induced epitope retrieval was accomplished for c-MYC using a steamer and EDTA with pH of 8.0 for 30 minutes, followed by a 5-minute cool down. Next, the slides were placed in Dako wash solution and then in the Dako autostainer. For detection of c-MYC, the slides were incubated in the first primary antibody c-MYC (Epitomics; clone Y69, catalog 1472-1, dilution 1:100) for 30 minutes, followed by incubation in a MACH 3 Rabbit Probe (Biocare Medical) for 20 minutes, a MACH 3 Rabbit Polymer (Biocare Medical) for 20 minutes, and chromagen DAB+(DakoCytomation) for two 5-minute incubations. The slides were then counterstained in hematoxylin, dehydrated,

TABLE 5

Clinical characteristics of patients with SMM whose PB plasma underwent assessment of TCA metabolite concentrations

|         | Age | Gender | BMPC % | FISH              | S-phase | Glutamine | 2-HG | a-KG |
|---------|-----|--------|--------|-------------------|---------|-----------|------|------|
| SMM #1  | 64  | M      | 25     | N/A               | N/A     | 216.12    | 0.88 | 0.61 |
| SMM #2  | 66  | M      | 30     | Del 13            | 0       | 445.27    | 0.79 | 0.27 |
| SMM #3  | 58  | M      | 20     | N/A               | 0       | 415.46    | 0.98 | 0.23 |
| SMM #4  | 46  | M      | 50     | N/A               | 0       | 479.74    | 0.71 | 0.30 |
| SMM #5  | 66  | M      | 50     | N/A               | 1.4     | 494.18    | 0.72 | 0.28 |
| SMM #6  | 73  | F      | 50     | N/A               | 0.8     | 454.50    | 0.54 | 0.21 |
| SMM #7  | 67  | F      | 15     | del13, t(4; 14)   | 1       | 403.50    | 0.82 | 0.25 |
| SMM #8  | 66  | M      | 40     | del 17p, trisomies| 0.9     | 108.29    | 0.74 | 6.42 |
| SMM #9  | 82  | M      | 30     | trisomies         | 1       | 204.39    | 0.43 | 3.99 |
| SMM #10 | 72  | F      | 20     | del13, del14      | N/A     | 408.73    | 0.37 | 7.44 |
| SMM #11 | 53  | M      | 20     | N/A               | 0.6     | 532.67    | 0.64 | 1.08 |
| SMM #12 | 60  | F      | 20     | del13, t(4; 14)   | 0.4     | 409.08    | 0.83 | 0.22 |
| SMM #13 | 56  |        | 30     | N/A               | 0.2     | 487.31    | 1.23 | 0.41 |
| SMM #14 | 53  | M      | 40     | N/A               | 0.4     | 463.70    | 0.72 | 0.36 |
| SMM #15 | 81  | M      | 30     | N/A               | 0.4     | 322.57    | 4.63 | 1.32 |
| SMM #16 | 61  | M      | 15     | t(4; 14)          | 0.2     | 384.33    | 0.41 | 0.92 |
| SMM #17 | 65  | M      | 15     | N/A               | N/A     | 450.06    | 0.63 | 1.33 |
| SMM #18 | 53  | F      | 15     | N/A               | 0       | 479.85    | 1.25 | 0.95 |
| SMM #19 | 40  | M      | 10     | N/A               | N/A     | 551.71    | 0.49 | 4.63 |
| SMM #20 | 42  | M      | 10     | del 13, t(6; 14)  | 0.4     | 365.72    | 0.94 | 0.25 |
| SMM #21 | 61  | M      | 15     | trisomies         | 0.1     | 409.44    | 0.41 | 0.29 |
| SMM #22 | 67  | F      | 10     | N/A               | 0.4     | 419.78    | 0.49 | 0.93 |
| SMM #23 | 60  | F      | 10     | N/A               | 0       | 477.96    | 0.61 | 0.19 |
| SMM #24 | 58  | M      | 10     | N/A               | 0.4     | 472.23    | 0.65 | 11.6 |
| SMM #25 | 70  | M      | 20     | trisomy 11        | 0       | 264.31    | 0.72 | 4.4  | cleared in xylene, and coverslipped. Appropriate positive controls were used. The number of PCs expressing c-MYC in their nucleus was counted and scored as a percentage of the total PC population by 2 hematopathologist reviewers independently and then re-reviewed together to arrive at a uniform scoring of nuclear c-MYC expression.
Results
2-HG Levels in the BM Supernatant of Patients with SMM Correlates with the Percentage of BM PCs Expressing c-MYC.

Figure 5A:
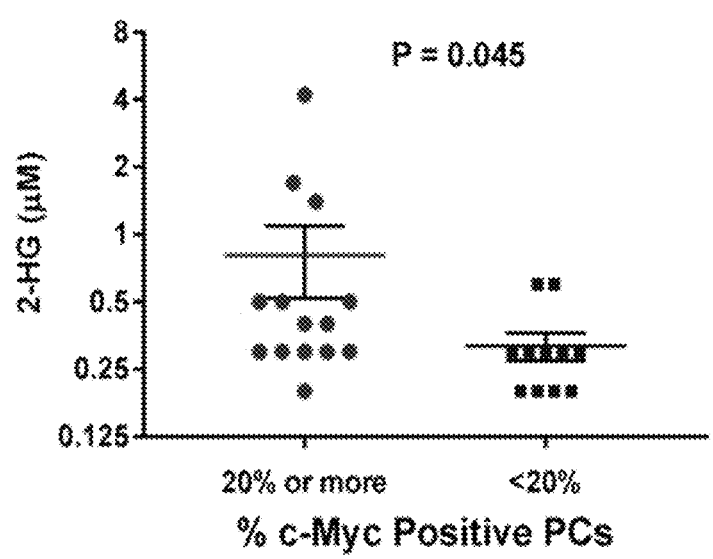
FIG. 5A is a dot plot graph depicting the individual (red circles and blue squares), mean (red and blue line), and ±SEM (black error bars) of 2-hydroxyglutarate (2-HG) concentrations in the BM supernatant of patients with smoldering multiple myeloma (SMM) whose BM biopsies show either ≥20% (n=14) or <20% (n=11) clonal plasma cells with c-MYC nuclear staining. Comparisons were made by the Mann-Whitney test, and significance was defined as P<0.05.
Figure 5B:
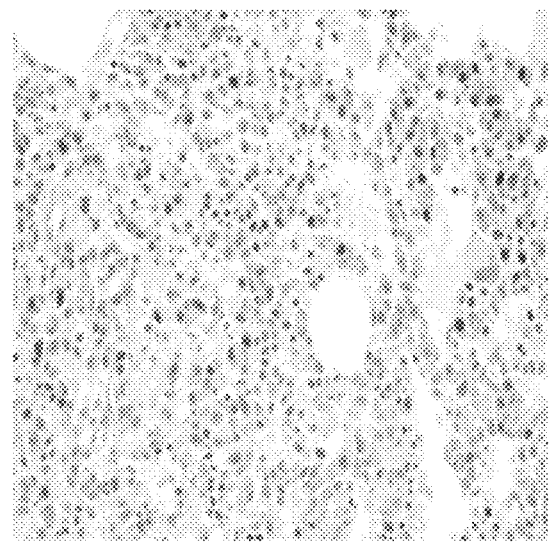
FIG. 5B is a photograph of an example of a BM biopsy (magnification 40×) showing >20% clonal plasma cells with c-MYC nuclear staining (brown).
Figure 5C:
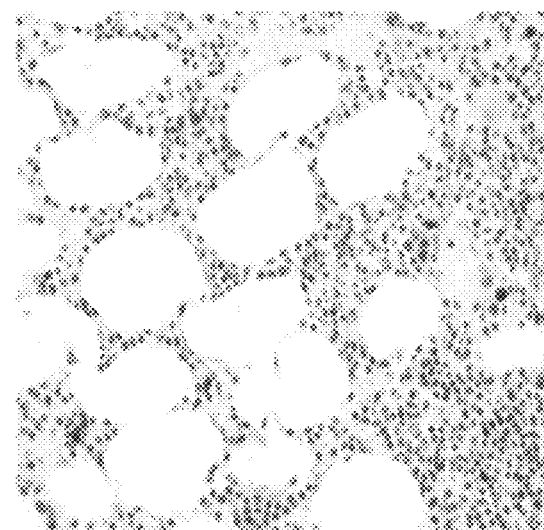
FIG. 5C is a photograph of an example of a BM biopsy (magnification 40×) showing <20% clonal plasma cells with c-MYC nuclear staining (brown).

The archived BM core biopsy blocks from the aforementioned 25 patients with SMM whose BM supernatant was used to quantify 2-HG levels were obtained. The percentage of total BM PCs expressing the protein c-MYC in their nucleus is detailed in Table 6, along with the rest of the patient characteristics and corresponding 2-HG concentrations in their BM supernatant. All patients appeared to have at least some proportion of their BM PCs express c-MYC in their nucleus. The BM supernatant 2-HG concentrations were higher in patients who had a higher percentage of BM PCs expressing nuclear c-MYC (i.e., >20% of total PCs) as demonstrated in FIG. 5A (P=0.045). Examples of variable percentages of BM PCs from patients with SMM expressing nuclear c-MYC and their corresponding BM plasma 2-HG levels are depicted in FIGS. 5B and 5C. Expression of nuclear c-MYC in 20% or more of BM clonal PCs predicted for a shorter TTP to MM (HR, 4.27; 95% CI, 1.46-15.48; P=0.007).

These results demonstrate that c-Myc expression in BM plasma cells correlates with 2-HG levels in the BM supernatant.

Example 4: Assessing Precursor PC Disorders for Risk of Progression

A PB plasma sample or a BM plasma sample is obtained from a human having a precursor PC disorder (e.g., SMM or MGUS). The obtained sample is examined for the presence of an elevated level of 2-HG (e.g., greater than 0.70 µM in a PB plasma sample or greater than 0.30 µM in a BM plasma sample). In some cases, a MS assay (e.g., GC/MS) is performed to detect the presence of an elevated level of 2-HG. If an elevated level of 2-HG is detected in the sample, as compared to a control level (e.g., the median level of 2-HG typically observed in a sample from one or more humans having the precursor PC disorder), then the human is identified as being at risk for progressing to MM.

Example 5: Treating High-Risk Precursor PC Disorders

A PB plasma sample or a BM plasma sample is obtained from a human having a precursor PC disorder (e.g., SMM or MGUS). The obtained sample is examined for the presence of an elevated level of 2-HG (e.g., greater than 0.70 µM in a PB plasma sample or greater than 0.30 µM in a BM plasma

TABLE 6

Clinical characteristics of patients with SMM whose bone marrow supernatant underwent assessment of TCA metabolite concentrations

| Patient # | Age | Gender | BMPC % | Glutamate µM | 2-HG µM | α-KG µM | % PCs w/ c-Myc expression | TTP (months) | OS (months) |
|---|---|---|---|---|---|---|---|---|---|
| SMM #1 | 55 | F | 50% | 28 | 0.4 | 5.5 | 20 | 7 | 63 |
| SMM #2 | 68 | F | 15% | 70 | 0.5 | 8.4 | 30 | 6 | 88# |
| SMM #3 | 38 | M | 20% | 133 | 0.2 | 4.4 | 10 | 107* | 126# |
| SMM #4 | 64 | M | 25% | 127 | 1.4 | 6.1 | 30 | 7 | 118# |
| SMM #5 | 66 | M | 30% | 199 | 1.7 | 9.3 | 50 | 12 | 103 |
| SMM #6 | 57 | M | 15% | 64 | 0.2 | 7.7 | 30 | 14 | 108# |
| SMM #7 | 57 | M | 10% | 243 | 0.3 | 11.6 | 10 | 114* | 138# |
| SMM #8 | 64 | F | 30% | 158 | 0.3 | 5.6 | 10 | 69 | 151# |
| SMM #9 | 66 | M | 50% | 58 | 0.5 | 6.6 | 50 | 9 | 107# |
| SMM #10 | 67 | F | 15% | 86 | 0.6 | 9.6 | 10 | 12 | 13 |
| SMM #11 | 30 | F | 30% | 299 | 0.6 | 3.3 | 10 | 122* | 144# |
| SMM #12 | 66 | M | 40% | 61 | 0.5 | 7.0 | 30 | 2 | 47# |
| SMM #13 | 82 | M | 30% | 32 | 0.3 | 6.7 | 20 | 11 | 48# |
| SMM #14 | 72 | F | 20% | 48 | 0.3 | 8.4 | 50 | 5 | 59# |
| SMM #15 | 71 | M | 10% | 39 | 0.3 | 5.7 | 10 | 62* | 68# |
| SMM #16 | 54 | F | 15% | 403 | 0.2 | 0.3 | 10 | 7 | 59 |
| SMM #17 | 61 | M | 15% | 42 | 0.3 | 5.0 | 40 | 57 | 96# |
| SMM #18 | 60 | F | 10% | 74 | 0.3 | 8.0 | 30 | 68* | 86# |
| SMM #19 | 79 | M | 50% | 42 | 4.2 | 6.9 | 20 | 3 | 50# |
| SMM #20 | 60 | F | 20% | 31 | 0.3 | 7.0 | 10 | 8 | 45 |
| SMM #21 | 61 | M | 15% | 36 | 0.4 | 6.3 | 40 | 60* | 90# |
| SMM #22 | 67 | F | 40% | 195 | 0.3 | 0.6 | 20 | 6 | 83 |
| SMM #23 | 62 | F | 30% | 76 | 0.3 | 7.2 | 10 | 58* | 84# |
| SMM #24 | 80 | F | 50% | 37 | 0.2 | 5.5 | 10 | 19 | 45 |
| SMM #25 | 42 | M | 10% | 61 | 0.2 | 4.9 | 10 | 51* | 78# |

*Did not progress to MM at last follow up

Alive at last follow up sample). In some cases, a MS assay (e.g., GC/MS) is performed to detect the presence of an elevated level of 2-HG. If an elevated level of 2-HG is detected in the sample, as compared to a control level (e.g., the median level of 2-HG typically observed in a sample from one or more humans having the precursor PC disorder), then the human is administered one or more c-Myc inhibitors and/or one or more MM treatments. The administered MM treatment(s) and/or c-Myc inhibitor(s) can slow or prevent the progression of a high-risk precursor PC disorder to MM.

Example 6: Treating High-Risk Precursor PC Disorders

A human identified as having elevated levels of 2-HG (e.g., greater than 0.70 µM in a PB plasma sample or greater than 0.30 µM in a BM plasma sample) is administered one or more c-Myc inhibitors and/or one or more MM treatments. The administered MM treatment(s) and/or c-Myc inhibitor(s) can slow or prevent the progression of a high-risk precursor PC disorder to MM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining if a monoclonal gammopathy of undetermined significance (MGUS) or a smoldering multiple myeloma (SMM) in a mammal is likely to progress to a multiple myeloma, said method comprising:
identifying said mammal as having greater than 0.30 µM of 2-hydroxyglutarate (2-HG) within a biological sample from said mammal, and
administering a multiple myeloma treatment to said mammal, wherein said multiple myeloma treatment is selected from the group consisting of lenalidomide, carfilzomib, dexamethasone, daratumumab, and elotuzumab, wherein said treatment is effective to slow development of a symptom of a multiple myeloma.

2. The method of claim 1, wherein said administering said multiple myeloma treatment is effective to slow development of a complication associated with said MGUS or said SMM, and wherein said complication associated with said MGUS or said SMM is selected from the group consisting of frequent infections, bone pain, thinning bones, broken bones, kidney failure, anemia, thrombocytopenia, neutropenia, and hypercalcemia.

3. The method of claim 1, further comprising administering a c-Myc inhibitor to said mammal.

4. The method of claim 3, wherein said c-Myc inhibitor is a siRNA.

5. The method of claim 3, wherein said c-Myc inhibitor is an inhibitor of glutamine metabolism.

6. The method of claim 5, wherein said inhibitor of glutamine metabolism is a glutaminase inhibitor.

SEQUENCE LISTING

```
<160> NUMBER OF SEQ ID NOS: 3

<210> SEQ ID NO 1
<211> LENGTH: 21
<212> TYPE: RNA
<213> ORGANISM: Homo sapiens

<400> SEQUENCE: 1
gccacagcau acauccuguu u                                                   21

<210> SEQ ID NO 2
<211> LENGTH: 19
<212> TYPE: RNA
<213> ORGANISM: Homo sapiens

<400> SEQUENCE: 2
ggucagaguc uggaucacc                                                      19

<210> SEQ ID NO 3
<211> LENGTH: 19
<212> TYPE: RNA
<213> ORGANISM: Homo sapiens

<400> SEQUENCE: 3
gaugaggaag aaaucgaug                                                      19
```

7. The method of claim 1, wherein said mammal is a human.

8. The method of claim 1, wherein said biological sample is peripheral blood (PB) plasma or bone marrow (BM) plasma.

9. The method of claim 8, wherein said biological sample is PB plasma, and wherein said PB plasma comprises greater than 0.70 µM 2-HG.

10. The method of claim 8, wherein said biological sample is BM plasma, and wherein said BM plasma comprises greater than 0.30 µM 2-HG.

\* \* \* \* \*